(12) United States Patent
Khan et al.

(10) Patent No.: US 9,902,686 B2
(45) Date of Patent: Feb. 27, 2018

(54) MULTIPHASE REACTOR SYSTEM

(71) Applicant: National University of Singapore, Singapore (SG)

(72) Inventors: Saif A. Khan, Sinagpore (SG); Swee Kun Yap, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 15/342,686

(22) Filed: Nov. 3, 2016

(65) Prior Publication Data

US 2017/0121271 A1    May 4, 2017

Related U.S. Application Data

(60) Provisional application No. 62/285,591, filed on Nov. 3, 2015.

(51) Int. Cl.
| | |
|---|---|
| B01J 8/00 | (2006.01) |
| B01J 8/02 | (2006.01) |
| B01J 8/04 | (2006.01) |
| B01J 8/06 | (2006.01) |
| B01J 19/00 | (2006.01) |
| B01J 19/24 | (2006.01) |
| C07C 209/36 | (2006.01) |
| C07C 209/00 | (2006.01) |
| C07C 209/30 | (2006.01) |
| C07C 209/32 | (2006.01) |

(52) U.S. Cl.
CPC .......... *C07C 209/36* (2013.01); *B01J 8/0492* (2013.01); *B01J 8/065* (2013.01); *B01J 19/2425* (2013.01); *B01J 2208/06* (2013.01); *B01J 2219/0254* (2013.01); *B01J 2219/0277* (2013.01); *B01J 2219/0295* (2013.01)

(58) Field of Classification Search
CPC ........ B01J 8/00; B01J 8/02; B01J 8/04; B01J 8/0492; B01J 8/06; B01J 8/065; B01J 19/00; B01J 19/24; B01J 19/2415; B01J 19/2425; B01J 2208/06; B01J 2219/02; B01J 2219/025; B01J 2219/0277; B01J 2219/0295; C07C 209/00; C07C 209/30; C07C 209/32; C07C 209/36
See application file for complete search history.

(56) References Cited

U.S. PATENT DOCUMENTS 7,214,320 B1 * 5/2007 Gregori ............ B01L 3/502753
                                                            210/143
2017/0101358 A1    4/2017  Khan et al.

FOREIGN PATENT DOCUMENTS

ES              2443821 A1 *   2/2014

OTHER PUBLICATIONS

English translation of ES 2443821 A1, published on Feb. 20, 2014.*
Al-Rawashdeh et al "Design Criteria for a Barrier-Based Gas-Liquid Flow Distributor for Parallel Microchannels" Chemical Engineering Journal vol. 181, pp. 549-556, 2012.

(Continued)

*Primary Examiner* — Natasha Young
(74) *Attorney, Agent, or Firm* — Cesari and McKenna, LLP

(57) ABSTRACT

A one-to-many parallelized millireactor system capable of high throughput production in millireactors. Also disclosed is a method for carrying out multi-phase reactions.

15 Claims, 27 Drawing Sheets

(56) References Cited

OTHER PUBLICATIONS

Al-Rawashdeh et al "Design Methodology for Barrier-Based Two Phase Flow Distributor" American Institute of Chemical Engineers Journal vol. 58, pp. 3482-3493, 2012.
Al-Rawashdeh et al "Phenylacetylene Hydrogenation Over [Rh(NBD)(PPh$_3$)$_2$]BF$_4$ Catalyst in a Numbered-Up Microchannels Reactor" Industrial and Engineering Chemistry Research vol. 52, pp. 11516-11526, 2013.
Kreutzer et al "Multiphase Monolith Reactors: Chemical Reaction Engineering of Segmented Flow in Microchannels" Chemical Engineering Science vol. 60, pp. 5895-5916, 2005.
Masterflex Peristaltic Pumps, Cole Parmer Product Catalog p. 1223, 2014.
VersaGrad Binary Gradient Pumps, Scientific Systems Inc.
Woitalka et al "Scalability of Mass Transfer in Liquid-Liquid Flow" Chemical Engineering Science vol. 116, pp. 1-8, 2014.
Yue et al "Gas-Liquid-Liquid Three-Phase Flow Pattern and Pressure Drop in a Microfluidic Chip: Similarities with Gas-Liquid/Liquid-Liquid Flows" Lab on a Chip vol. 14, pp. 1632-1649, 2014.

* cited by examiner

MULTIPHASE REACTOR SYSTEM

CROSS-REFERENCE TO RELATED APPLICATIONS

This application claims the priority to U.S. Provisional Application No. 62/285,591, filed on Nov. 3, 2015, the content of which is hereby incorporated by reference in its entirety.

The present invention relates to a multiphase reactor system. In particular, the present invention relates to a one-to-many parallelized millireactor system is designed for high throughput production in millireactors.

Gas-liquid multiphase catalytic reactions such as oxidation, hydrogenation and halogenation are integral to the pharmaceutical and fine chemical industries. These reactions involve the contacting of gases, liquids and solids, and are conventionally carried out in stirred batch reactors, at high stirring rates and under harsh reaction conditions of elevated temperature and pressure to overcome severe heat and mass transfer limitations. The use of micro/millireactors for reactions such as multiphase organic syntheses offers numerous advantages such as accelerated heat and mass transfer as well as greater control over reaction conditions compared to macro-scale reactors such as large stirred tank reactors. Continuous-flow microreactors offer tremendous heat and mass transport acceleration, in addition to the prospect of facile phase separation, and are of considerable interest as platforms for conducting multiphase reactions in recent years. Several demonstrations of biphasic organic syntheses in various microreactor configurations have reported significant improvements in product yield, selectivity and reaction times. For example, gas-liquid segmented flow, in which the gaseous reactant and the liquid plug containing the substrate and the catalyst flow alternately, provides direct contact between the two phases with enhanced interfacial gas-liquid mass transfer. Membrane microreactors have also been used as platforms for biphasic organic syntheses by allowing for the independent infusion of gaseous and liquid phase reactants. We have previously introduced a triphasic segmented flow reactor for rapid nanoparticle-catalyzed reactions, where the compartmentalization of catalyst in a separate immiscible fluid phase allows facile catalyst recovery and recycle, and the provision of a large interfacial area for the dissolution of gaseous reactant enables an order of magnitude reduction in the reaction time compared to batch reactors. We have demonstrated the application of this reactor scheme in the hydrogenation of a variety of substrates, using different catalysts, with enhanced yields and selectivities under near ambient conditions. These advantages notwithstanding, the productivity of single micro-/millifluidic reactors is limited by their low volumetric throughputs.

The exploitation of micro/millireactor technologies for larger production volumes can be achieved by a combination of scaling up, i.e. an increase in reactor dimensions to the 'milli' scale or 'meso' scale, to the extent possible without sacrificing the accelerated interphase heat and mass transport properties, and scaling out, i.e. the operation of multiple identical reactors in parallel.

However, the volumetric throughput per reactor is limited for these small-scale flowing reactors. Consequently, high throughput syntheses using micro/millireactor requires the operation of multiple identical reactors in parallel. Since peristaltic pumps are preferred over syringe pumps due to the ability of the former to continuously withdraw feedstock from a large reservoir, issues of flow rate pulsations in the liquid feedstreams are inevitable. These pulsations dramatically influence the stability of the multiphase flow in the parallelized millireactor system. In addition to the need to ensure a smooth feedstream, there is also a need to ensure an even distribution of feed into each of the individual reactor operating in parallel. The combination of these two engineering challenges, if not adequately addressed, can ultimately lead to reactor failure.

There are two crucial engineering challenges in the design and operation of a parallelized multiphase flow reactor system. The first crucial challenge is the equal routing of the multiple fluid phases into the various arms of the parallelized flow network that is immune to variations or temporal fluctuations in pressure drop in any of the individual branches. Even distribution of fluids into a parallelized reactor system by means of pressure-drop (or 'barrier') channels as flow distributors has been well demonstrated for both gas-liquid and liquid-liquid reactor networks. The basic idea is for the distributor channels to have fluidic resistances much greater than those of the reactor channels; the high pressure drop across these distributor channels is thus able to effectively diminish the effects of any fluctuations or variations in pressure drop within the arms of the reactor network.

The second crucial challenge is to have uninterrupted, smooth, and pulse-free delivery of all fluids supplied to the network. While syringe pumps are often the preferred choice for the operation of single micro/millireactors due to their ability to provide fluid flow at a constant volumetric flow rate, the finite capacities of syringes limit the use of these pumps in continuous long-term production. Uninterrupted flows can be achieved by means of pumps that are able to continuously withdraw feed from a reservoir, such as peristaltic pumps, high performance liquid chromatography (HPLC) pumps and displacement pumps, among others. However, these pumps introduce both periodic and aperiodic pressure pulsations into the fluid streams, resulting in the injection of feed with time varying flow rates into the reactor network. When left unresolved, such pressure pulsations dramatically influence the stability of a multiphase reactor network, since the morphology of multiphase flows (i.e. the observed flow regimes) in small scale flowing reactors is typically highly sensitive to small changes in flow conditions.

There are two general approaches to address the issue of flow pulsations—passive capacitance-based flow regulation and active regulation via the use of mass flow controllers (MFCs) and/or the integration of complex control algorithms with the pumping hardware. The use of passive capacitance-based damping has been applied in the engineering of large, 'macroscale' fluid flow networks; typical dampers consist of an assembly of capacitances and resistances in series, with pipes of suitable length and diameter acting as hydraulic resistors, and vessels with a gaseous headspace above the flowing liquid serving as pneumatic capacitors, or devices with variable pressure-dependent volumes (e.g. elastic walls) acting as hydraulic capacitors. However, both general approaches have drawbacks that limit their use in complex micro-/millifluidic reactor networks involving multiphase flows. Thus, for example, the passive approaches typically involve large dead volumes, as in the case of pneumatic dampers, while active approaches involve flow through complex geometries, which dramatically increases the possibility of fouling, especially for the flow of solid suspensions (such as colloidal nanoparticle catalysts as used in our work). Furthermore, while the latter is able to provide active regulation in simple flow circuits, its ability to regulate highly branched and multiphase flow networks with time-varying feed flow rates is limited, and increases in complexity with the number of fluid phases fed into the system.

In addition to the above, there are several drawbacks to current microreactors for gas-liquid reactions. First, catalyst recovery and recycle remains a challenge, especially where the products, unreacted starting materials, and catalyst coexist in the same liquid phase. Moreover, catalyst deactivation shortens the shelf life of the reactors. Finally, the rate of mass transport is limited for reactions beyond a biphasic setting, e.g., triphasic reactions.

There is a need to develop a new reactor system that does not have the above-mentioned drawbacks.

The listing or discussion of an apparently prior-published document in this specification should not necessarily be taken as an acknowledgement that the document is part of the state of the art or is common general knowledge.

Any document referred to herein is hereby incorporated by reference in its entirety.

Here, in the present invention, a quantitative fluidic circuit-based design framework for parallelized multiphase micro-/millifluidic reactor networks that combines resistance-based fluid distribution and capacitance-based autonomous flow regulation that overcomes the key challenges highlighted above is presented. The paper is divided into two parts. First, the design of fluid supply manifolds in a general multiphase micro-/millfluidic reactor network, where a simple, passive capacitance-based method allows autonomous damping of both periodic and aperiodic flow pulsations in combination with the resistance-based strategy for flow distribution, is presented. We derive and present a model for the dynamics of fluidic damping, and validate it with experiments on model pulsed flows; the availability of a model for the damping dynamics also sheds light on important network-level design considerations. In the second part of the paper, this framework is applied to present the first demonstration of an eight-fold parallelized triphasic segmented-flow reactor system for platinum nanoparticle-catalyzed hydrogenations of nitrobenzene, a model substrate, with continuous catalyst recovery and online recycle.

As such, the present invention relates to a reactor system containing multiple millireactors, each of which includes a millitube and three feed lines. Each feed line forks or branches out to many feed lines, i.e. on a "one-to-many" principle. In particular, each feed line forks into two feed lines (bifurcate), and these in turn forks into two further feed lines each. In an embodiment, a single feed line branches out from one to eight feed lines. Unexpectedly, the reactor system exhibits (i) tremendous mass transport acceleration in catalytic organic syntheses and (ii) facile catalyst recovery and recycle.

We present a design framework for the robust, self-regulating long-term operation of parallelized multiphase microfluidic reactor networks without the use of any active flow control elements. A fluidic circuit-based design scheme is developed for the feed manifolds in a general multiphase microfluidic reactor network where an inline, fluidic capacitance element allows autonomous damping of periodic and aperiodic flow disturbances, in combination with a fluidic resistance-based strategy for even flow distribution into the network. A dynamic model for the fluidic capacitance element is derived, numerically solved and validated with experiments on model time varying feed flows. This model sheds new light on important network-level design considerations for stable long-term operation. Finally, our design scheme is applied to present the first demonstration of a robust eight-fold parallelized three-phase segmented-flow reactor network for platinum nanoparticle-catalyzed hydrogenation of nitrobenzene, a model substrate, at an approximately constant substrate conversion of ~80% under ambient conditions, with continuous online recovery and recycle of the colloidal catalyst phase over five hours of operation.

In particular, the work herein also describes in detail a method for overcoming the above mentioned challenges. An embodiment of how the designed parallelized system can be used is in the nanoparticle-catalyzed hydrogenation of nitrobenzene, a model pharmaceutical substrate, in triphasic millireactors. The parallelized system yields a consistent conversion of (83±6.7)% across all eight reactors over the course of several hours, with a product throughput of 9.6 mL/h. Finally, we demonstrate continuous catalyst recovery and recycle, where the aqueous PtNPs are subsequently continuously recycled. The application of a robust and general scheme for the parallelization of triphasic flows for an industrially relevant application demonstrates the feasibility of implementing the designed system in sustainable pharmaceutical manufacturing.

In a first aspect of the present invention, there is provided a multiphase reactor system for performing multi-phase reactions, the reactor system comprising:

(a) a plurality of millitube reactors, each millitube reactor comprises a first end, a second end, a first chamber attached to the first end, and a second chamber disposed between the two ends of the millitube;

(b) a first feed line comprising a first end and a second end, the first end for receiving a first liquid, a first level junction connected to the second end, and a first hydraulic damper disposed between the two ends of the first feed line;

(c) a second feed line comprising a first end and a second end, the first end for receiving a second liquid, a first level junction connected to the second end, and a second hydraulic damper disposed between the two ends of the second feed line;

(d) a third feed line comprising a first end and a second end, the first end for receiving a gas, and a first level junction connected to the second end, wherein,
(a) the first level junction in each of the first, second and third feed line forks each feed line into y-number of feed lines,
(b) each of the y-number of feed lines from the first level junction of the first feed is connected in fluid communication with the first chamber of the millitube reactor, each of the y-number of feed lines from the first level junction of the second feed is connected in fluid communication with the second chamber, and each of the y-number of feed lines from the first level junction of the third feed is connected in fluid communication with the third chamber,
(c) the first chamber of the millitube reactor is capable of receiving both the first and second liquids, and the second chamber is capable of receiving both a gas and a mixture of the first and second liquids
(d) y is an integer greater or equal to 2.

As such, each of the first, second and third feed lines may be forked, branched or split into y-number of lines after or downstream the hydraulic damper. In an embodiment of the invention, each feed line is initially forked into two feed lines at the first level junction. It is understand that any number, e.g. two, three, four etc., feed lines may be forked out from the first level junction.

In an embodiment, each of the feed lines further comprises a second level junction downstream the first level junction for forking each feed line into two further feed lines. Again, the forked feed lines from the second level junction further comprise a third level junction for forking each feed line into two further feed lines.

In particular, there can be any number of junctions to fork or branch the feed lines further to any number. For example, there can be any n-level junctions for providing a plurality of first, second and third feed lines connected in fluid communication with a plurality of millitube reactors, the plurality of millitube reactors connected in parallels, wherein n is an integer greater or equal to 1.

Similarly, downstream the reactor once the reaction is completed at the second end of the millitube reactors, these second ends converge into one output stream. In particular, junctions are available for converging every two output streams into one until a single output stream conducting the products is formed. This single output stream conducts the product of the reaction to a reservoir or container. As such, the reactor system can further include four containers: a first liquid container, a second liquid container, a gas container, and an outflow container.

The multiphase reactor system may further comprise:
(a) a first liquid container connected to the first end of the first feed line, the first container connected in fluid communication to a first pump;
(b) a second liquid container connected to the first end of the second feed line, the second container connected in fluid communication to a second pump;
(c) a gas container connected to the first end of the third feed line; and
(d) an outflow container connected to the second end of the millitube.

In an embodiment, the first and second pumps are each a peristaltic pump.

The feed lines, conduits, tubes in the system may be of any suitable dimensions. The millitube reactor may also be of any suitable dimensions.

The term "millitube" herein refers to a tube that has an inner diameter of 0.5 to 10 mm, e.g., 1 to 5 mm. Typically, the millitube has a length of 1 to 50 m, e.g., 2 to 20 m. It can be made of various materials, such as polytetrafluoro-ethylene, polyether ether ketone, fluorinated ethylene propylene, glass, and metal. During the operation, the tube surface is wetted by an organic phase. In an embodiment, the millitube reactor has a length of about 2 to 20 m and an inner diameter of about 1 to 5 mm.

In an embodiment, the hydraulic damper comprises a first tube, a second tube, and a third tube that are connected in series, the second tube having an inner diameter larger than that of the first tube and that of the third tube. The first tube has the same length and inner diameter as those of the third tube. In an embodiment, the second tube is an elastic sleeve and has an inner diameter of 4.76 mm and a length of 8 cm. It may be made of any suitable elastic material. In an embodiment, the second tube is made of silicone.

The length and diameter of the hydraulic damper may be of any suitable dimension. It is the combination of the length, diameter and damper material that will give its corresponding damping effect, which can be calculated theoretically, as will be demonstrated later in the document. The exact length and diameter of the hydraulic damper required depends on the pulsations introduced into the system via the pump or any disturbance source(s), the acceptable flow rate fluctuations, the damper material as well as the corresponding length and diameter of the tube(s) or network of tubes at both ends of the hydraulic damper.

In a second aspect of the present invention, there is provided a method for carrying out multi-phase reactions, the process comprising:
(a) preparing a first feed line for conducting a first liquid, a second feed line for conducting a second liquid containing the liquid reactant, and a third feed line for conducting a gas containing the gas reactant, the first liquid and the second liquid being immiscible;
(b) damping the first and second liquids in the first and second feed lines;
(c) forking the first, second and third feed lines into two feed streams, each feed stream connected in fluid communication with a millitube reactor; and
in a millitube reactor:
  (a) mixing the first liquid with the second liquid to form a two-phase mixture;
  (b) mixing the gas with the two-phase mixture to form a three-phase mixture;
  (c) reacting the liquid reactant, the gas reactant, and the catalyst to form a product; and
  (d) collecting the product formed.

As described earlier, each of the forked feed streams is further forked into two feed streams, each feed stream connected in fluid communication with a millitube reactor. Similarly, the method further comprises converging the output streams from the millitube reactor into one output. For example every two output streams downstream the millitube is converged or combined into one stream at a junction. Again, this stream is then combined with another stream until a single output is formed to conduct the product of the reaction to a reservoir container.

In an embodiment, the method further comprises dispersing or dissolving a catalyst in the first liquid. The gas contains, in addition to the gas reactant, a carrier gas, the gas reactant being $H_2$, CO, $O_2$, $F_2$, or $Cl_2$, and the carrier gas being $N_2$ or Ar.

In order that the present invention may be fully understood and readily put into practical effect, there shall now be described by way of non-limitative examples only preferred embodiments of the present invention, the description being with reference to the accompanying illustrative figures.

Figure 1:
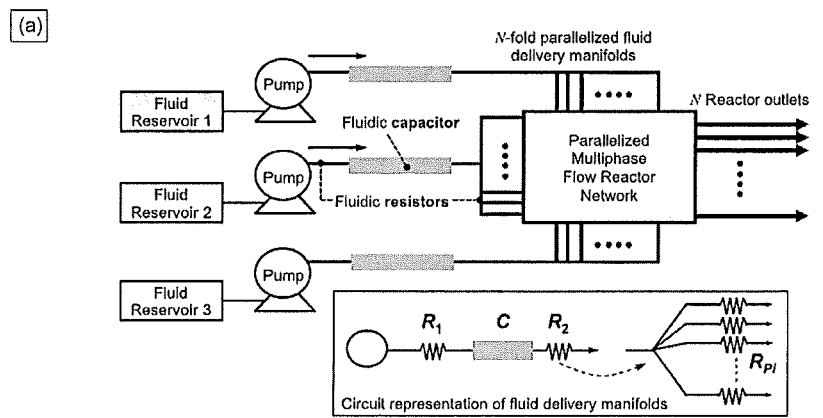
FIG. 1. (a) Schematic of a general multiphase microreactor network, indicating the N-fold parallelized fluid delivery manifolds. Each fluid delivery manifold is an assembly of inline fluidic resistors (narrow diameter tubes with rigid walls) and capacitors (large diameter tubes with flexible walls); details of the manifold construction are provided in Section 5 below. (Boxed inset) Circuit representation of each fluid delivery manifold, where the N-fold branched delivery lines, each having a fluidic resistance $R_{Pi}$, are represented by an effective resistance $R_2$. This is subsequently referred to as the $R_1$-C-$R_2$ schema (further details in Sections 2-4 below). (b) Schematic of the one-to-eight numbered-up triphasic segmented flow reactor network for metal-catalysed gas-liquid reactions. Inset illustrates the formation of triphasic flow in each reactor, at two T-junctions ($T_1$ and $T_2$) in series; a biphasic aqueous-organic segmented flow is first formed at $T_1$, followed by the injection of gas at $T_2$ to form a triphasic segmented flow.
Figure 1:
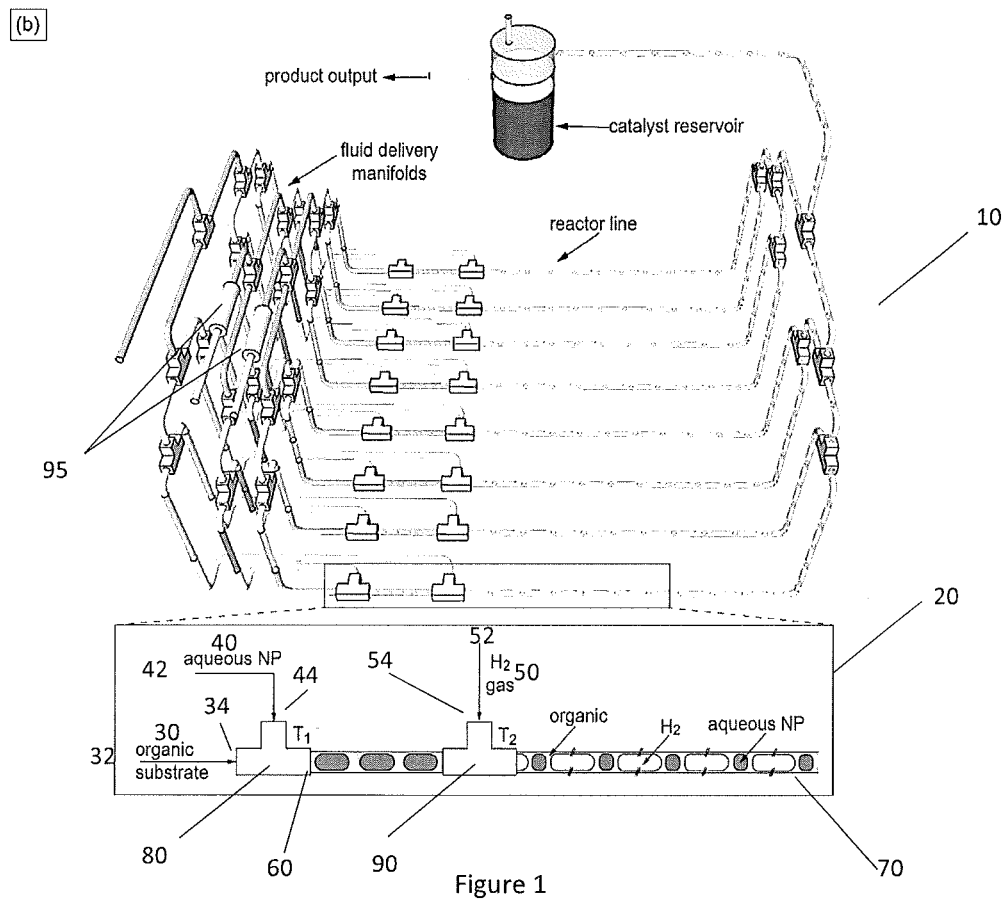

Within this invention is a reactor system containing multiple millireactors for conducting multiphasic flow reactions.

Referring to FIG. 1(b), the multiphase reactor system 10 comprises a plurality of millitube reactors 20 (as can be seen in the exploded inset). Each millitube reactor 20 has three feed lines, i.e. a first feed line 30, a second feed line 40, and a third feed line 50. The millitube reactor 20 may be any suitable size. In an embodiment, it is 1 mm to 5 mm in inner diameter and 2 m to 20 m in length, has a first end 60, a second end 70, a first chamber 80 ($T_1$) attached to the first end 60, and a second chamber 90 ($T_2$) disposed between the two ends thereof. The first feed line 30 has a first end 32 for receiving a first liquid (in an embodiment, an organic substrate liquid), a second end 34 connected to the first chamber 80. The second feed line 40 has a first end 42 or receiving a second liquid, a second end 44 connected to the first chamber 80. The third feed line 50 has a first end 52 for receiving a gas and a second end 54 connected to the second chamber 90.

Not shown in FIG. 1, each of the first, second and third feed lines may be forked, branched or split into y-number of lines after or downstream the hydraulic damper. In an embodiment of the invention, each feed line is initially forked into two feed lines at the first level junction. It is understood that any number, e.g. two, three, four etc., feed lines may be forked out from the first level junction. FIG. 1 shows an example of each feed line forking or splitting into two feed lines. It is understood that any number of feed lines may be split or forked at a junction.

The reactor system 10 can further include a first liquid container, a second liquid container, a gas container, an outflow container, a catalyst reservoir, product output, a first pump, and a second pump. The first container for holding a first liquid is connected to the first pump and the first end of the first feed line. The second container for holding a second liquid is connected to the second pump and the first end of the second feed line. The gas container for holding a gas is connected to the first end of the third feed line. The outflow container for receiving a liquid mixture containing products is connected to the second end of the millitube.

In a typical reactor system, there are multiple parallel millitube reactors (e.g., eight) for rapid transitional metal-catalyzed gas-liquid reaction (e.g., hydrogenation) and the first and second pumps are each a peristaltic pump.

Figure 5:
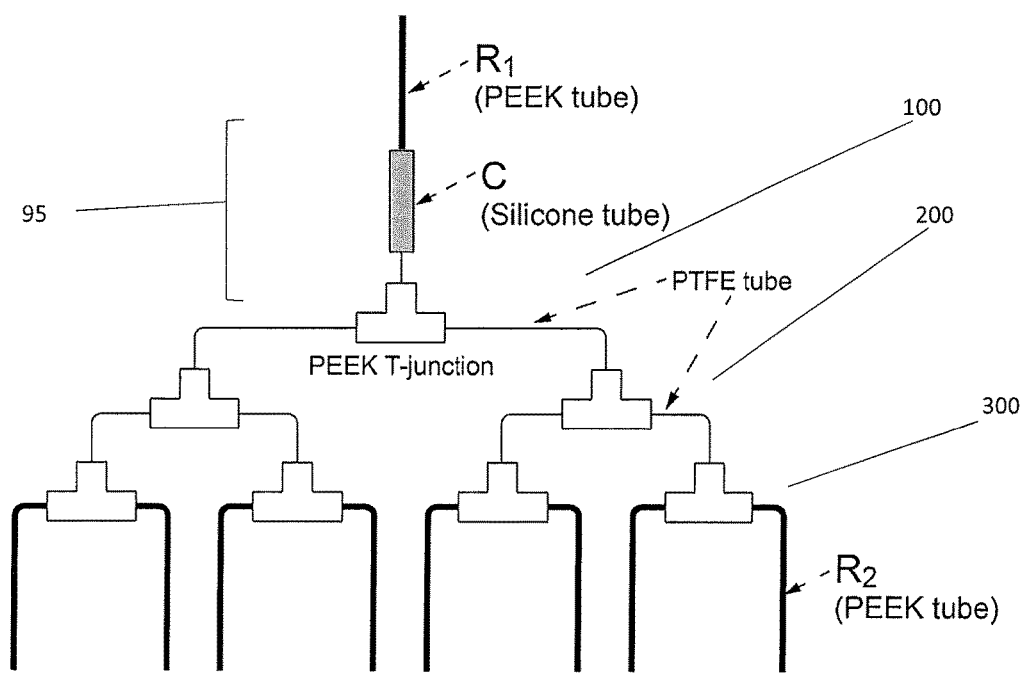
FIG. 5. Schematic of the two liquid delivery manifolds used in our three-phase reactor network.

Each of the first, second and third feed line forks into two feed lines. FIG. 5 shows a schematic diagram of a feed line. Generally, each feed line has a junction (e.g. T-junction) for forking each line into two (bifurcate). As seen in FIG. 5, there are three levels of junctions 100, 200, 300 for branching a single feed line into eight that are connected in parallel, i.e. one-to-eight millitube reactors. With each of the first and second feed lines, there is a master hydraulic damper 95 upstream the feed line. In particular, the hydraulic damper is disposed between the two ends of the single feed line before it even forks at the first level junction 100. There can be further levels of junctions to further provide a plurality of millitube reactors connected in parallel. In alternative embodiments, each junction may also fork or branch out three or more feed lines. For example, there can be any n-level junctions for providing a plurality of first, second and third feed lines connected in fluid communication with a plurality of millitube reactors, the plurality of millitube reactors connected in parallels, wherein n is an integer greater or equal to 1. As such, the feed reactants are damped upstream prior to the first forking or branching in the first level junction.

Figure 12:
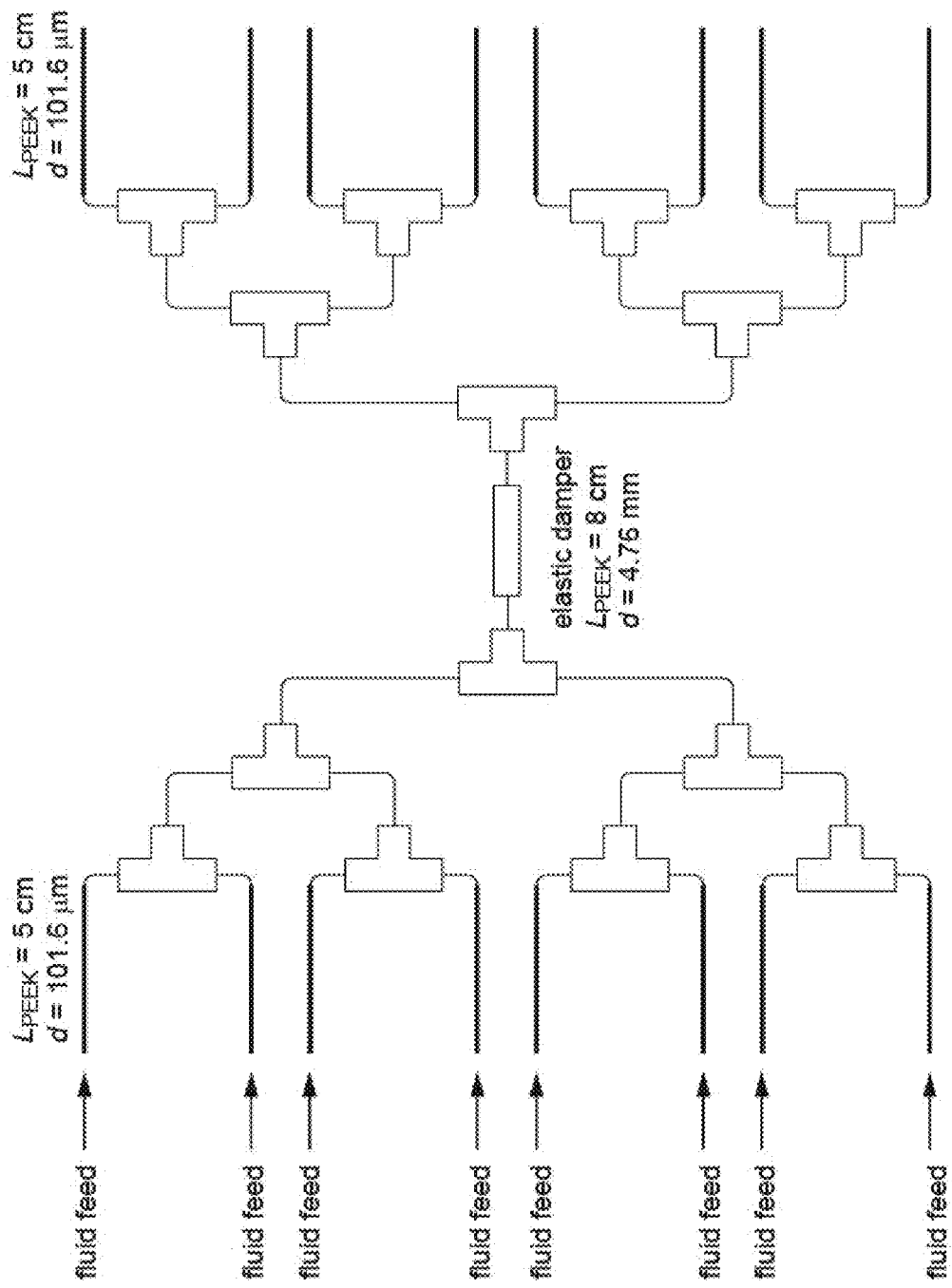
FIG. 12. Schematic of the application of an inline hydraulic damper for a network of fluid flow. Here, an example of the dimensions of the network of fluid flow is given but not limited to, the specifications described above.

Alternatively, as shown in FIG. 12, there could be a plurality of feed lines that converge prior to entering the hydraulic damper and then fork or branch out into a plurality of feed lines, each feed line feeding a millitube reactor.

Similarly, as shown in FIG. 1, downstream the reactor once the reaction is completed at the second end of the millitube reactors, these second ends converge into one output stream. In particular, junctions are available for converging every two output streams into one until a single output stream conducting the products is formed. This single output stream conducts the product of the reaction to a reservoir or container. As such, the reactor system can further include four containers: a first liquid container, a second liquid container, a gas container, and an outflow container.

Therefore, in an embodiment, there may be two master hydraulic dampers, one for the first feed line and another for the second feed line. The hydraulic dampers serve to damp out pressure fluctuations or flow rate fluctuations resulting from the peristaltic pumps, thereby allowing for formation of a smooth triphasic flow in all millireactors.

An exemplary hydraulic damper consists of three tubes connected in series, namely, a first tube, a second tube, and a third tube. Preferably, the first tube and the third tube have the same length and same inner diameter, and these two tubes have their length and inner diameter smaller than that of the second tube. For instance, the hydraulic dampers each consist of a first tube of 50 mm in length and 0.1 mm in inner diameter, a second tube of 80 mm in length and 4.8 mm in inner diameter, and a third tube of 50 mm in length and 0.1 mm in inner diameter in series. Each of the three tubes can be a polytetrafluoroethylene tube, a silicone tube, or a viton tube. It is preferred that the second tube is an elastic tube (e.g., a silicone tube or a viton tube).

Also within this invention is a process for conducting a triphasic flow reaction that requires a liquid reactant, a gas reactant, and a catalyst.

Described in detail below is an exemplary process for performing such a flow reaction using a reactor system set forth above.

A first liquid is prepared by dispersing or dissolving a catalyst in a first solvent. The homogeneous solution thus prepared is stored in a first liquid container. A second liquid can be a neat liquid reactant or produced by dissolving a liquid reactant in a second solvent immiscible with the first solvent and stored in a second liquid container. Both the first and second liquids are drawn from the two liquid containers by peristaltic pumps into the first and second feed lines as shown in FIG. 1b, respectively. The first and second liquids are mixed in the first chamber to form a two-phase mixture of first liquid spheres and the second liquid A gas containing a carrier gas and a gas reactant is transported via the third feed line and mixed with the two-phase mixture in the second chamber to form in the millitube a three-phase mixture, which contains first liquid segments, the second liquid, and gas bubbles. The gas bubbles can be elongated by controlling the gas pressure or the gas flow rate, thus enlarging the interacting surface areas between the gas and the second liquid containing the liquid reactant so as to accelerate mass transport of a reaction. The mass transport within the reaction phase is also accelerated by reducing the second liquid (e.g., organic) segments into thin films, with a thickness of the films ranging from 0.01 to 1 mm. The reaction between the liquid reactant and the gas reactant in the presence of the catalyst then takes place to form a product, which is subsequently collected in an outflow container.

The catalyst used in this process is dispersed or dissolved in the first solvent to form a homogeneous solution. Examples of the first solvent include but are not limited to water, methanol, ethanol, isopropanol, tetrahydrofuran, diethyl ether, heptane, isopropyl acetate, isopropyl amine, acetic acid, and NN-diisopropylethylamine. The second solvent can also be, among others, water, methanol, ethanol, isopropanol, tetrahydrofuran, diethyl ether, heptane, isopropyl acetate, isopropyl amine, acetic acid, or NN-diisopropylethylamine. Importantly, the two solvents are immiscible with each other. The gas can be a pure gas reactant (e.g., $O_2$) or a mixture of a carrier gas (e.g., Ar) and a gas reactant (e.g., $H_2$).

To ensure a stable flow in the reactor system, it is important that the flow rate of the gas far exceeds that of the liquid phases. The ratio of the gas flow rate to each of the liquid flow rates is, preferably, 20-100 and, more preferably, 30-100. The process of this invention can tolerate a gas pressure of 10 kPa to 5000 kPa (e.g., 101-103 kPa) and a reaction temperature of −150° C. to 500° C. (e.g., 25° C.).

In an exemplary process of hydrogenation of 1-hexene, the catalyst is rhodium nanoparticles each having a diameter of about 3 nm. Referring back to FIG. 1b, the first liquid, prepared by dispersing the rhodium nanoparticles in water, is introduced via the first feed line at 20 $\mu$lmin$^{-1}$ into the first chamber. Simultaneously, the second liquid, prepared by dissolving 1-hexene in cyclohexane, is introduced via the second feed line at 10 $\mu$lmin$^{-1}$ into the first chamber to mix with the first liquid to form a biphasic liquid mixture. The hydrogen gas at near atmospheric pressure, e.g., 101-103 kPa, is introduced via the third feed line at a flow speed of about 29 mm/s into the second chamber to mix with the biphasic liquid mixture to form a triphasic mixture containing gas bubbles at room temperature. Hydrogenation of 1-hexene in the presence of the rhodium nanoparticles subsequently takes place to produce the product hexane. Unexpectedly, the hydrogenation of 1-hexene using a millireactor is about 30 folds faster than that using a batch reactor, demonstrating tremendous mass transport acceleration achieved in a reactor system of this invention.

A quick comparison between the reactor system of this invention and commercial microreactors reveals that for the hydrogenation of a double bond (C=C) the millireactor is able to achieve catalyst activity at least 60% higher than that of similar hydrogenation conducted in fixed bed microreactors. Following an exemplary process of this invention, the activity of platinum nanoparticles (PtNPs), a catalyst, for hydrogenation of nitrobenzene, is 110 min$^1$ (see Example 2 below), which is twice that achieved by PtNPs immobilized on the walls of a conventional microreactor.

The catalyst used in the triphasic flow reactor system of this invention can be continuously recycled. In one example, a platinum nanoparticle catalyst is unexpectedly recovered and recycled almost to the full extent over the course of 5 hours as evidenced by insignificant loss of its substrate conversion rate.

Figure 10:
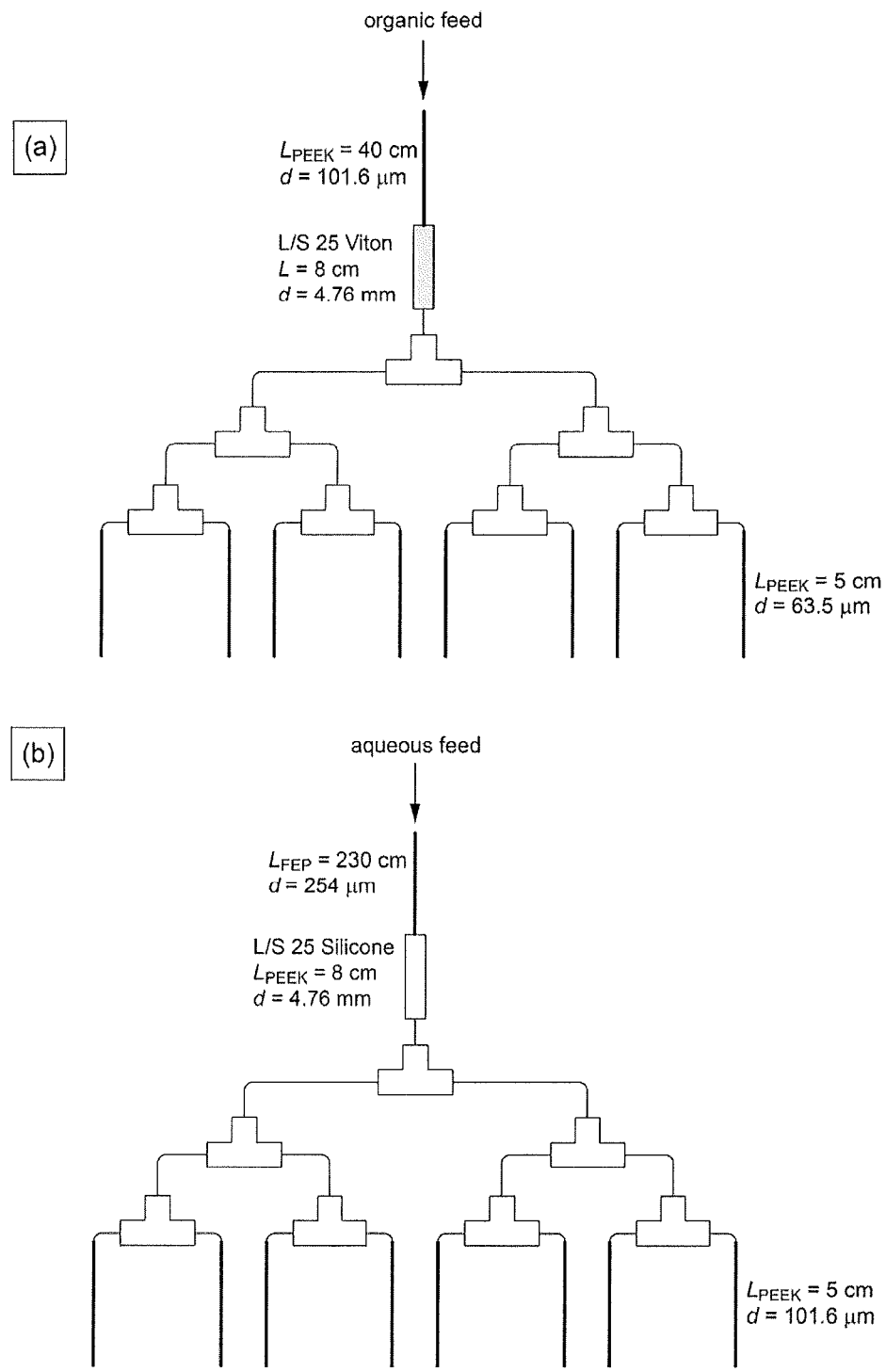
FIG. 10. Schematic of a parallelized fluid distributor with a single inline hydraulic damper for each fluid distributor. Here, an example of (a) an organic feed stream and (b) an aqueous feed stream are given respectively. The same setup can be applied for any fluctuating fluid flow.
Figure 11:
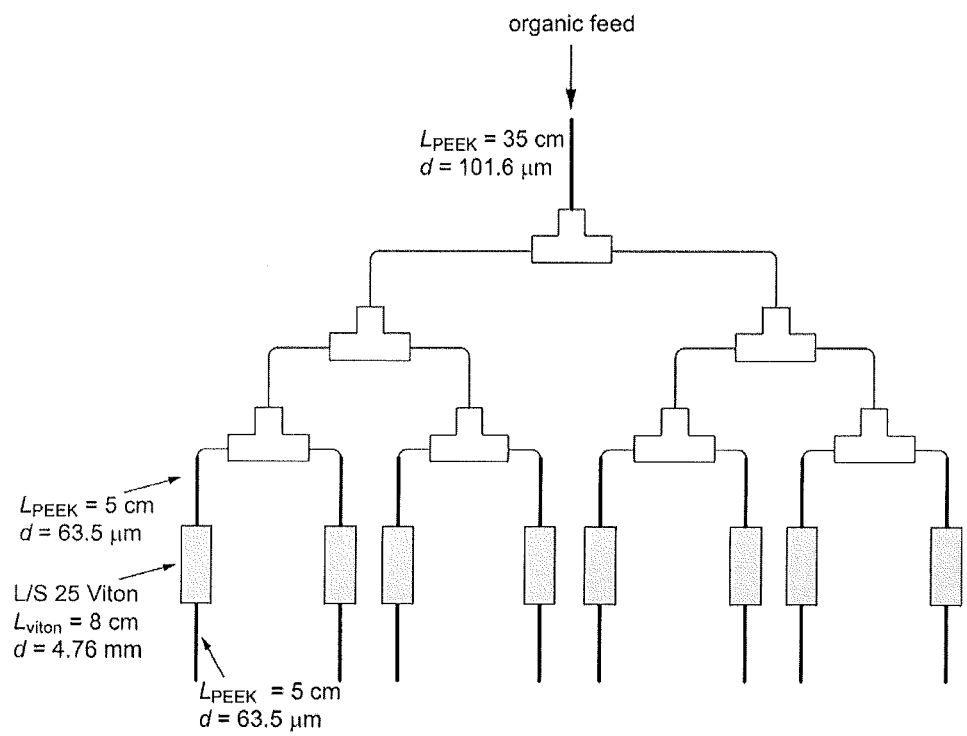
FIG. 11. Schematic of a parallelized fluid distributor with an inline hydraulic damper in each of the parallelized stream. Here, an example of an organic feed stream is given. The same setup can be applied for any fluctuating fluid flow.

In the parallelization of any system involving fluid flow, the even distribution of fluids into each of the units operating in parallel is required. Consequently, for the operation of millireactors in parallel, fluid distributors must be designed to allow for the even distribution of fluids into each of the millireactor operating in parallel. In many cases, the pump used for fluid delivery introduces pulsations into the fluid stream, which may result in flow instability, particularly for multiphase systems. Previously, a one-to-many parallelization of triphasic millireactor with inline hydraulic dampers have been designed to damp out these pulsations introduced by the pump. However, in the designed mentioned therein, each parallel stream in the fluid distributor for the parallelized setup requires the incorporation of an inline hydraulic damper (FIG. 10). In this new design, only a single hydraulic damper is required in each fluid distributor, resulting in a drastic simplification of the parallelized millireactor system (FIG. 11). The simplification of this current design includes benefits such as reduced dead volume, simplification of engineering design and millireactor system operation, lower startup and shutdown time, higher ease of reactor system maintenance compared to the previous design.

In addition, in the design of the previous inline hydraulic damper, the design is restricted to sandwiching an elastic tube between two other tubes with significant hydraulic resistance. In the design of this new inline hydraulic damper, such limitation is not required. The inline hydraulic damper can thus be generalized for usage in a network of streams. The requirement for the proper functioning of the hydraulic damper can be generalized to have significant hydraulic resistance in the network of tubes/channels before and after the elastic tube which functions as the damper (FIG. 12).

EXAMPLE 1

Materials and Methods
1. Fluidic Damper Assembly and Testing.

Two different elastic tubes, each of 4.76 mm inner diameter (ID), were used in the construction of simple capacitance-based fluidic damping schemes—(i) polytetrafluoroethylene (PTFE) tube (Cole Parmer, 6.35 mm OD) and (ii) #25 silicone tube (Masterflex, 7.94 mm OD). The fluidic damper consisted of a 5 cm long 101.6 $\mu$m ID polyether ether ketone (PEEK) tube, an 8 cm long 4.76 mm ID elastic tube followed by another 5 cm long 101.6 $\mu$m ID PEEK tube assembled in series. Water was infused into the series of tubes by means of a peristaltic pump (Leadfluid BT-50S, YZ-15) at an average flow rate of ~267 $\mu$L/min and a liquid flow meter (Sensirion, SLI-1000) connected at the end of the fluidic damper was used to measure the variation of liquid flow rate with time.

2. Fluid Distribution Manifold Assembly and Testing.

A one-to-eight fluid delivery manifold incorporating a fluidic capacitance-based damping strategy was used to supply the two liquids (organic substrate and aqueous catalyst) into our reactor network. In both cases, 0.5 mm ID PEEK T-junctions were used at all bifurcations in the fluid lines. The gas distributor did not include a damper, and simply consisted of eight parallel 15 cm long 63.5 $\mu$m ID PEEK tubes assembled by successive bifurcations of the delivery line. Liquid flow distributors were designed as follows. The aqueous phase distributor consisted of a 230 cm long 254 µm ID fluorinated ethylene propylene (FEP) tube connected to an 8 cm long 4.76 mm ID silicone tube prior to branching by bifurcation into eight parallel lines, each consisting of a 5 cm long 101.6 µm ID PEEK tube. Similarly, the organic phase distributor consisted of a 40 cm long 101.6 µm ID PEEK tube connected to an 8 cm long 4.76 mm ID viton tube prior to branching into eight parallel lines consisting of a 5 cm long 63.5 µm ID PEEK tube. To calibrate the gas lines, flow rate of nitrogen gas (Soxal, purified) was measured via the water displacement method in an inverted 50 mL burette. Nitrogen gas was introduced into the main line, and the volume of water displaced by nitrogen gas in each parallel line within 5 min was then measured. The volumetric flow rate for the respective line was subsequently calculated. The aqueous lines were calibrated by infusing ultrapure water into the aqueous distributor at a gauge pressure of 1.31 atm using a peristaltic pump and measuring the average flow rate in each of the eight lines. The calibration of the organic lines was similarly carried out by infusing diisopropyl ether at a gauge pressure of 1.33 atm using a peristaltic pump into the organic phase distributor and measuring the mass of diisopropyl ether (Sigma, ≥98.5%) dispensed into individual vials at the outlets over time. An average flow rate of 40 µL/min and 20 µL/min was achieved for each of the lines in the aqueous and the organic distributor respectively.

3. Platinum Nanoparticle (PtNP) Synthesis.

PtNPs were synthesized using a classical ethanol-water reduction method. Briefly, 5 mM PtNP stock solution was prepared by refluxing 5 mM of $H_2PtCl_6 \cdot xH_2O$ (Sigma, 99.9% trace metal basis) and 2.775 g of polyvinylpyrrolidone (Alfa Aesar, M.W. 40 k) as the stabilizer in 30 mL of absolute ethanol (Fischer, ≥99.5%) and 20 mL of ultrapure water (Milli-Q, 18.2 MΩ·cm at 25° C.) at 135° C. for 45 min. Thereafter, all solvent was vaporized at 45° C. under reduced pressure to afford a black residue before adding 50 mL of ultrapure water to obtain a 5 mM stock solution containing ~3 nm PtNPs. The 5 mM stock solution was then further diluted to 0.5 mM prior to its use in hydrogenation reactions.

4. Hydrogenation in the Reactor Network.

Hydrogenation of nitrobenzene catalyzed by PtNPs was carried out in the millireactor system as follows: 100 mM of nitrobenzene in diisopropyl ether, 0.5 mM PtNPs and hydrogen gas were infused into each 30 m long, 1 mm ID millireactor at a rate of 20 µL/min, 40 µL/min and 2.9 mL/min respectively at near ambient conditions. Samples were collected periodically at the outlet of each millireactor over the course of approximately five hours, and the composition of the top organic product phase was analyzed via gas chromatography (Shimadzu 2010Plus). During shutdown, water and diisopropyl ether were flowed into the aqueous and organic flow distributors respectively at the same flow rate as that used in the reaction in order to flush out any residual catalysts and substrates in both the liquid flow distributors and the millireactors. During the 2 hour flushing, the flow of hydrogen gas into the millireactors was maintained in order to facilitate both the flushing of the millireactor and to prevent the backflow of liquids into the gas lines.

Results and Discussion

1. Multiphase Microreactor Network Layout

FIG. 1(a) is a schematic depiction of the elements of a general multiphase microreactor network, where three (or generally more) different fluids are delivered to a parallelized bank of microreactors via branched fluid delivery manifolds drawing fluid from their respective reservoirs via pumps (for gases, the reservoir and pump are replaced by a pressurized gas tank). FIG. 1(b) is a drawing of the assembled triphasic segmented flow reactor network used for nanoparticle-catalyzed hydrogenations, described further in Sections 6-8. From a fluidic circuit point of view, each fluid delivery manifold in the system has, in general, the following elements: (i) a fluidic resistor ($R_1$), (ii) a fluidic capacitor (C) and (iii) a branched system of N parallel resistors (N being the degree of parallelization), which are represented by an effective resistance ($R_2$), in exact analogy with electrical circuits. A 'resistor' in our work simply refers to a narrow diameter fluid delivery tube with nominally rigid walls, while a 'capacitor' is a wide diameter tube with flexible (elastic) walls. As will be discussed in detail below, this general schema for the fluid delivery manifold is able to not only distribute the fluid equally into each arm of the microreactor network, but is also able to effectively damp any pressure/flow fluctuations arising from the pumping mechanism autonomously, without requiring any active control mechanisms. In Sections 2-5 below, we present the design and analysis of the fluid delivery manifolds in detail, starting first from the simple $R_1$-C-$R_2$ schema of FIG. 1; sections 2-4 focus primarily on this theoretical scheme that provides the basis for design of the fluid distribution manifolds, and on insights obtained from the analysis of this scheme.

Figure 2:
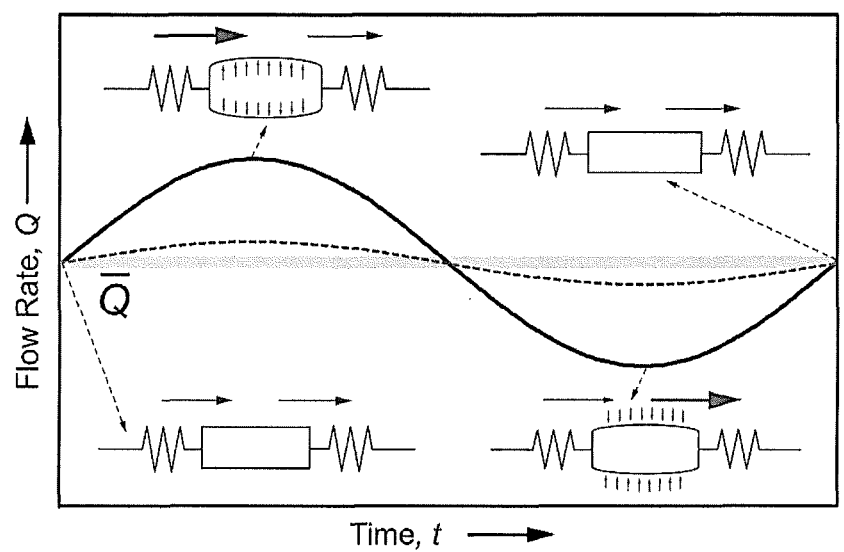
FIG. 2. Schematic illustrating the damping mechanism in the $R_1$-C-$R_2$ schema in response to a periodic time-varying upstream pressure. The solid line represents the periodic flow rate at the inlet of the series of tubes, while the dotted line indicates the corresponding instantaneous flow rate at the outlet.

2. $R_1$-C-$R_2$ Schema for Fluid Delivery—Qualitative Considerations for Capacitive Damping In the simplest form of the $R_1$-C-$R_2$ schema, the fluid delivery line is composed of an elastic tube sandwiched between two rigid tubes with narrow cross sections (and therefore high fluidic resistance). A qualitative picture of the mechanism by which such a scheme is able to damp out time varying fluctuations in the fluid delivery pressure is provided in FIG. 2. During cycles of high pressure, the gradually increasing flow of fluid (above its mean value) into the series of tubes leads to radial expansion of the elastic tube, to a degree which is dependent on the elasticity of the tube material. This expansion dynamically accommodates some of the excess incoming fluid, thereby damping the measured flow at the outlet. Likewise, an opposite effect is observed during cycles of low pressure, where the previously expanded elastic tube contracts, imposing a radial pressure that dynamically evacuates some of the accumulated fluid, thereby raising the outlet flow rate.

3. $R_1$-C-$R_2$ Schema for Fluid Delivery—Modeling and Validation

To quantitatively develop the above qualitative sketch, we use a simple dynamic model to describe the dependence of outlet flow rate in the $R_1$-C-$R_2$ schema on the dimensions and material of construction of the various components, in response to a time varying pressure provided by the upstream pumping mechanism. The simplest starting point for such a model is a periodic time-varying upstream pressure signal, $P_{pump}$, given by:

$$P_{pump}(t) = P_{mean}[1 + k\sin(\omega t)] \quad [1]$$

where $P_{mean}$ is the average pressure supplied by the pump, k is the fractional amplitude and ω the angular frequency of pressure pulsations. Next, to model the expansion of the elastic tube (capacitor 'C') in response to upstream pressure variations, a linearly elastic behavior is assumed, where the net radial stress $\sigma_{rr}$ exerted by the inner walls can be described by:

$$\sigma_{rr} = \kappa \frac{R_{i,1}(R_{i,2} - R_{i,1})}{R_{i,2}^2} \quad [2]$$

where $R_{i,1}$ and $R_{i,2}$ are the inner radius of the capacitor in its rest state and radially stretched state respectively, and $\kappa$ is the Young's modulus of elasticity of the tube material. Note that in this work, PEEK tubes are used as the resistors $R_1$ and $R_2$ that sandwich the capacitor, where each tube has a wall thickness more than fourteen times its inner radius. Furthermore, PEEK has a high elastic modulus of $\sim 10^9$ Pa. Thus, the rigid tube assumption is justified. The fluidic resistance R of each tube is obtained from the Hagen-Poiseuille equation, via the electric-hydraulic analogy, as:

$$R = \frac{128 \, \mu L}{\pi d^4} \quad [3]$$

where $\mu$ is the viscosity of the fluid flowing within the tube, and L and d are the length and inner diameter of the tube respectively. Finally, the instantaneous volumetric flow rate ($Q_{in}$) entering the series of tubes can be calculated as $$Q_{in}(t) = \frac{P_{pump}(t)}{R_1 + R_C + R_2} \quad [4]$$

where the hydraulic resistance $R_C$ of the capacitor tube used in our work is typically $\sim 10^6$ times smaller than $R_1$ and $R_2$, due to an $\sim 50$ times larger cross section.

The mathematical relationships of Equations [1]-[4] allow us to set up a simple discretized, quasi-steady calculation for the flow rate $Q_{out}$ at the outlet of the series of tubes. The calculation begins at 'baseline' conditions—i.e. with the upstream pressure at $P_{mean}$ and the capacitor at its rest radius, and move forward in time steps $\Delta t$ that are much smaller ($\sim 10^{-3} \times$) than the period of the pressure signal. Next, we assume that the elastic tube in the $R_1$-C-$R_2$ schema responds instantaneously to varying upstream pressure. Therefore, within each discrete time step, a recursive calculation for a quasi-steady outlet flow rate $Q_{out}$ is performed. This is done by recursively refining the estimate for the radial stress in the capacitor. For each time step, a first estimate for radial stress is obtained from the difference between the upstream pressure and the pressure drop across $R_2$:

$$\sigma_{rr} = P_{pump} - R_1 Q_{in} \quad [5]$$

In the above equation, the pressure drop across the capacitor is assumed to be negligible, which is reasonable in light of its large cross-sectional diameter (47 times larger than that of $R_1$ and $R_2$). From the Hagen Poiseuille equation, the pressure drop across a tube scales inversely to the fourth power of diameter, thereby rendering the pressure drop across the resistors, $R_1$ and $R_2$, $\sim 10^6$ times larger than that across the capacitor. The volumetric flow rates $Q_{in}$ and $Q_{out}$ can now be refined in a manner similar to Equation [6] as follows:

$$Q_{in} = \frac{P_{pump} - \sigma_{rr}}{R_1} \quad [6]$$

$$Q_{out} = \frac{\sigma_{rr}}{R_2}$$

The volume change of the capacitor is obtained by mass conservation, which in turn allows us to update its inner radius $R_{i,2}$ as follows:

$$\Delta V = (Q_{in} - Q_{out}) \Delta t \quad [7]$$

$$V_C^{new} = V_C^{old} + \Delta V \quad [8]$$

$$R_{i,2} = \sqrt{\frac{V_C^{new}}{\pi L_C}} \quad [9]$$

The radial stress is now updated with the new inner radius obtained above and using Equation [2], after which Equations [6]-[9] and [2] are recursively used until $Q_{out}$ converges to a nominally steady value for that time step.

Figure 3:
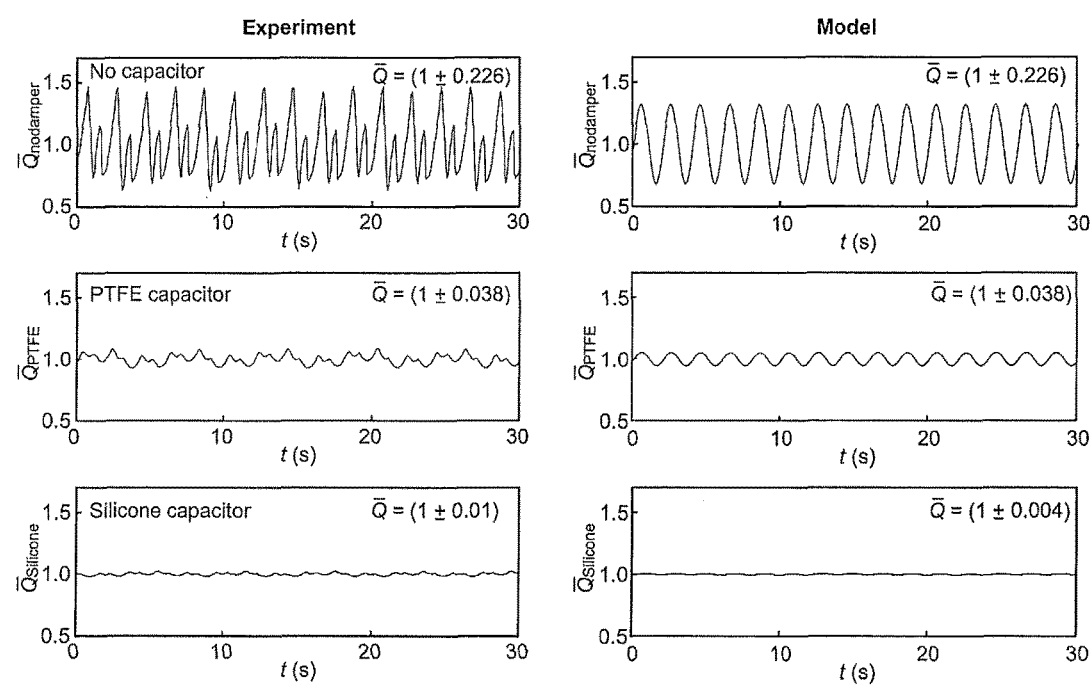
FIG. 3. Damping effectiveness of the $R_1$-C-$R_2$ schema—comparison between experiments conducted on a simple three-tube series configuration through which fluid is delivered by a peristaltic pump (details in text and experimental section) and model predictions. All graphs plot a normalized flow rate (relative to the average) at the outlet versus time; higher elasticity of the capacitor material in the $R_1$-C-$R_2$ schema clearly results in more effective pulse attenuation, in both experiments and model predictions.

Using water as a model fluid, the results from this simple model are first compared with the experiments on three different versions of the $R_1$-C-$R_2$ schema, in which an 8 cm long 4.76 mm ID capacitive tube of two different materials is sandwiched between two 5 cm long 101.6 μm ID PEEK resistor tubes. As seen in FIG. 3, the model predictions and experimental observations are found to be in excellent agreement with each other. In the control experiment ($R_1$-$R_2$ schema), severe flow rate pulsations are observed due to the peristaltic pump used. In contrast, when a PTFE capacitor with $\Lambda \sim 10^8$ Pa is used, a marked damping of the flow rate pulsations is observed, and when a highly elastic silicone-based capacitor ($\kappa \sim 10^6$ Pa) is used, the flow rate pulsations are damped even further to $\sim 1\%$ of the mean flow rate.

4. $R_1$-C-$R_2$ Schema for Fluid Delivery—Design Insights

Figure 4:
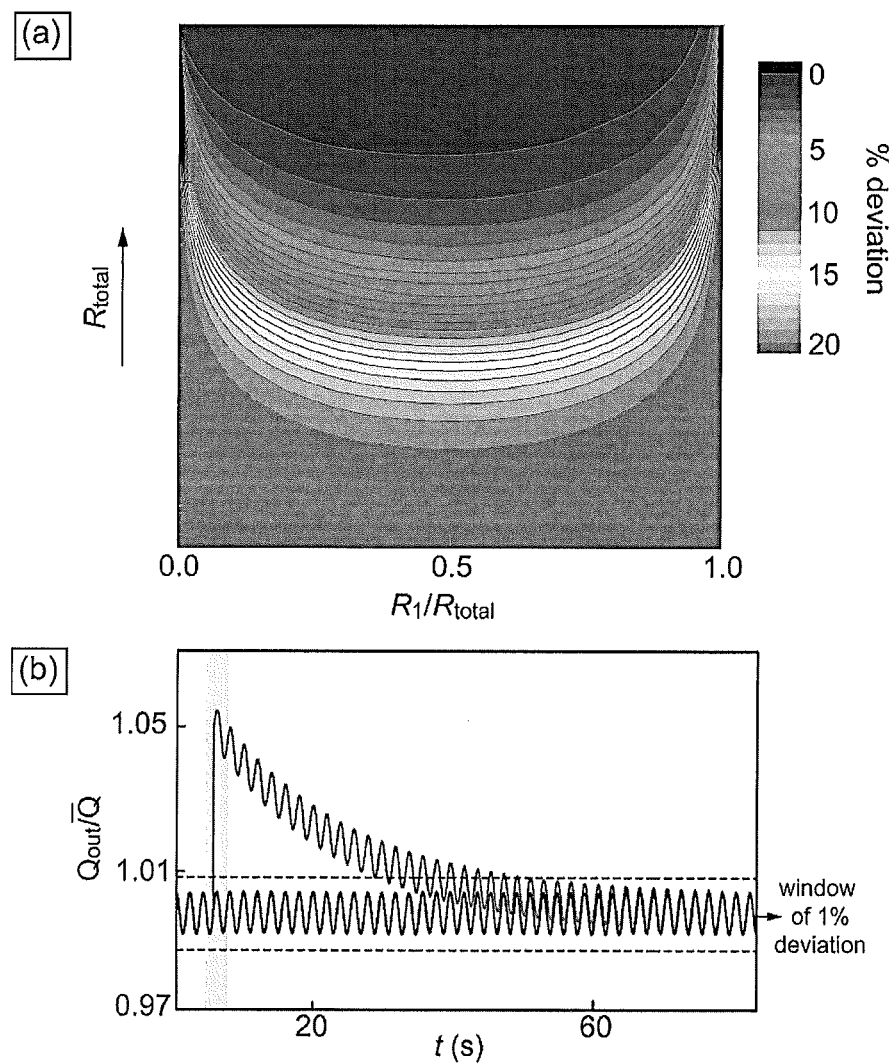
FIG. 4. (a) Contour plot of damping effectiveness (quantified as a percentage of deviation from the mean flow rate) against the total hydraulic resistance $R_{total}$ and the ratio $R_1/R_{total}$, where $R_{total}=R_1+R_2$ is the sum of hydraulic resistances placed on both ends of the elastic capacitor. The simulated conditions correspond to those of the silicone capacitor of FIG. 3 (details in experimental section) (b) Simulated dynamic response of the $R_1$-C-$R_2$ schema, plotted as a normalized volumetric outlet flow rate versus time, to two pulse disturbances of amplitude equal to and 100× the mean flow rate respectively, applied for 0.01 s within the shaded rectangle. The former causes a minimal disturbance to the outlet flow rate, while the latter leads to a rapidly decaying response with less than 6% deviation from the mean flow rate.

Upon validation of our model with simple experiments, we analyze it further to uncover important design insights. FIG. 4(a) is a contour plot of the degree of damping achievable in the $R_1$-C-$R_2$ schema, quantified as a percentage deviation from the mean flow rate, as a function of two parameters—the total resistance $R_{total}$ (=$R_1$+$R_2$), and the ratio $R_1/R_{total}$. Interestingly, it is observed that there exists an optimum configuration of $R_1 = 0.5 R_{total}$ for effective damping at every value of $R_{total}$. In other words, the $R_1$-C-$R_2$ schema is most effective when two equal resistors are placed at either end of the capacitor element. Thus, when $R_1/R_{total} \to 0$ (as in a C-R schema) or when $R_1/R_{total} \to 1$ (as in an R-C schema), the damping effectiveness approaches zero due to the lack of resistance to changes in flow rate at either ends of the elastic tube. This crucial design insight is further validated with experiments similar to those presented in FIG. 3 (see supporting information for details). Secondly, higher $R_{total}$ results in more effective damping of pulsations, which is intuitively in accord with the qualitative comments of Section 2; higher resistances allow effective trapping and release of fluid during cycles of high and low pressure respectively, via greater radial stress generated within the capacitor element.

Next, our model also highlights how the $R_1$-C-$R_2$ schema is not only able to damp out periodic pulsations introduced by pumps, but is also able to provide passive, autonomous regulation of flow rates in the presence of aperiodic temporal disturbances. FIG. 4(b) demonstrates the simulated dynamic response of a model $R_1$-C-$R_2$ configuration to a sharp pulse, of amplitude equal to the mean flow rate, superimposed onto a periodic time varying flow. The built-in damping from the capacitor is able to suppress the pulse disturbance nearly completely, with negligible disturbance in the outlet flow. Even more drastically, as shown in FIG. 4(b), when a sharp pulse of amplitude 100× greater than the mean flow rate is applied, the resulting disturbance in the outlet flow is less than 6%, and rapidly decays to the undisturbed state. The ability of the $R_1$-C-$R_2$ schema to provide excellent disturbance regulation is crucial to ensure robust and stable operation of a massively parallelized multiphase flow network, where the operating flow regime can be highly sensitive to the flow disturbances.

5. Fluid Delivery Manifold Design for the Reactor Network

A one-to-eight branched fluid delivery manifold built on the $R_1$-C-$R_2$ schema was used for both the aqueous and organic feed lines in our reactor network. Details of the manifold construction and calibration, including the dimensions of the various tubes are provided in the experimental section; here we simply highlight the key design features. As shown in FIG. 5, each manifold consists of a fluidic resistor $R_1$, followed by a capacitor C, which leads to a one-to-eight bifurcated network of parallel resistors, $R_{P,i}$. Such a fluid manifold has to satisfy two general design considerations. Firstly, each resistor $R_{P,i}$ has to have sufficient fluidic resistance to allow even distribution of fluid across the eight lines, as well as to allow the requisite damping of upstream flow pulsations. Secondly, as described in Section 4, it is crucial to ensure that the equivalent resistance $R_2$ of the branched distributor network is equal to the upstream resistor $R_1$, for maximized damping efficacy. Next, we observe that the pressure drop across the eight reactor channels is negligible compared to that in the fluid distribution lines, which effectively allows the decoupling of distributor design from the pressure drop characteristics of the individual reactors. The pressure drop across each microreactor is ~1 kPa, estimated from the corresponding single-phase laminar pressure drops of gas and liquid weighted by the volume fraction of the respective phases. Since the reactors are primarily filled with gas, this leads to an estimate for pressure drop that is an order of magnitude less than that across the flow distributor channels (~13 kPa), allowing us to ignore the hydraulic resistance of the reactor channels in designing the distributor network, as described below.

To obtain the dimensions for the various tubes comprising the distributor, the average gauge pressure $P_{avg}$ provided by the pump used for fluid delivery and the required flow rate Q for each of the eight parallel lines is first used to estimate the total fluidic resistance $R_{total}$ of the network, using once again the electric-fluidic analogy (Equation [10]).

$$P_{avg} = R_{total} Q_{total} \quad [10]$$

Where $Q_{total}=8Q$. With $R_{total}$ known, the hydraulic resistances $R_1$ and $R_2$ are both $0.5 R_{total}$. $R_{P,i}$ follows from the application of the formula for the effective resistance of a network of parallel resistances as:

$$\frac{1}{R_2} = \frac{2}{R_{total}} = 8 \frac{1}{R_{P,i}} \quad [11]$$

Finally, Equation [3] is used with the above designed values of $R_1$ and $R_{P,i}$ to select appropriate lengths and diameters of the various tubes in the network.

Finally, in the design of the gas flow distributor, a capacitor is not required since the gas is supplied by a constant pressure source—the gas cylinder. The required fluidic resistance for each of the eight parallel gas lines can then be calculated from Equations [10] and [11]. A compact gas phase distributor is then designed by incorporating short tubes with narrow inner diameter, since fluidic resistances scale inversely to the fourth power of diameter and to the power of one in length (Equation [3]).

6. Reactor Network Assembly, Testing and Startup Dynamics

Figure 6:
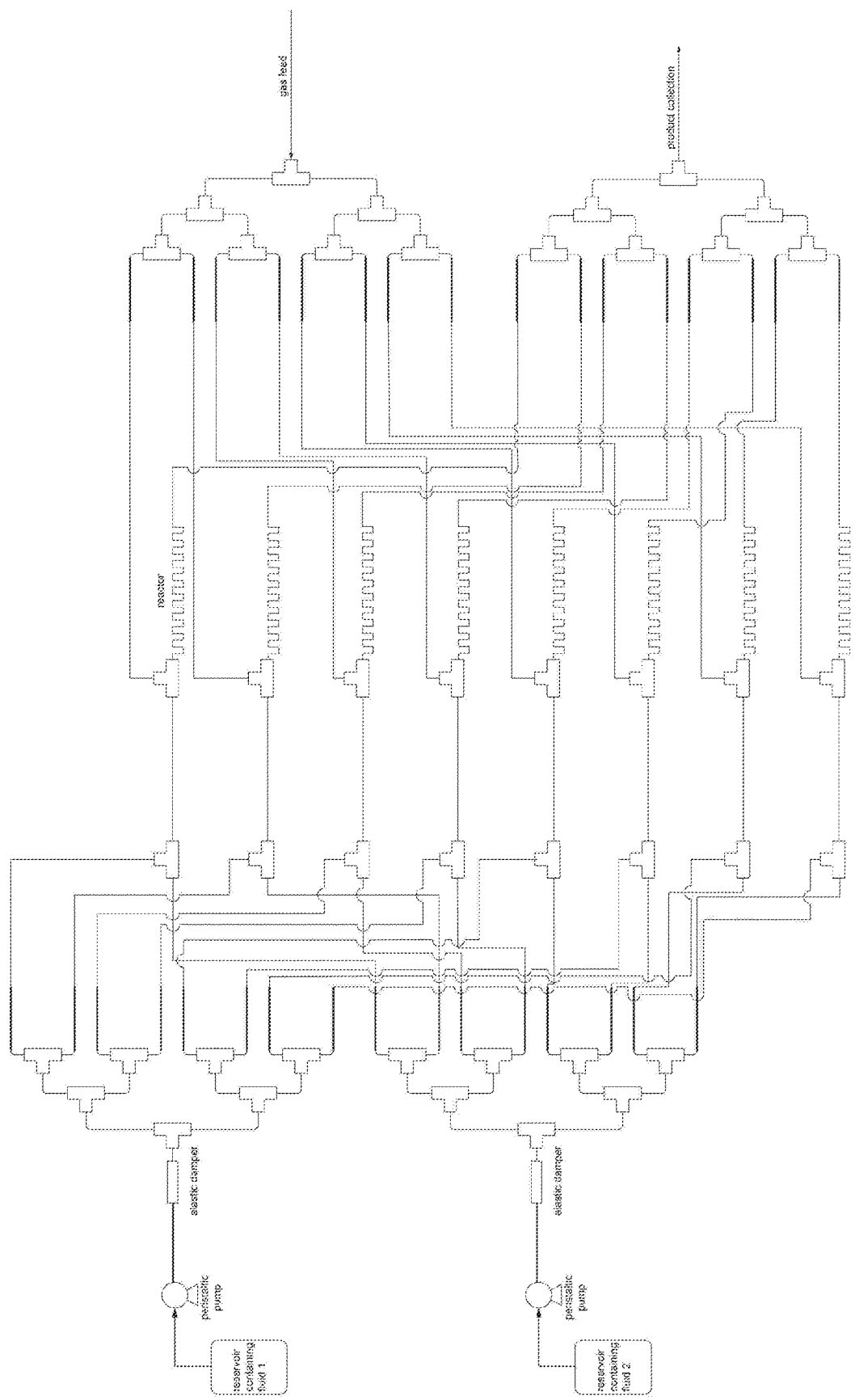
FIG. 6. Benchtop photograph of the assembled triphasic segmented flow reactor system FIG. 7. (a) High-speed stereomicroscopic images of triphasic flows in the eight parallel reactor lines, highlighting the consistency of flow pattern across the network. All scale bars represent 1 mm. (b) Normalized biphasic flow speeds ($\overline{U}_2$), and (c) normalized triphasic flow speeds ($\overline{U}_3$) obtained from image analysis of the high-speed flow visualization. (d) Comparison of nitrobenzene conversion across the eight parallel reactors, highlighting the consistency in substrate conversion in the parallelized system.

A one-to-eight fluid delivery manifold was designed for the three fluids—the gas, aqueous and organic phases—and assembled to form our eight-fold parallelized triphasic flow reactor network depicted schematically in FIG. 1(b). Prior to the implementation of the network for hydrogenation reactions, the startup dynamics, flow uniformity and stability were first assessed in the absence of reaction. To do so, water, diisopropyl ether and nitrogen gas were used as test fluids in the network. In starting up the parallelized reactor system, the flow of the various feed fluids into the system was initiated sequentially. Referring to FIG. 1(b), nitrogen gas at near ambient pressure was first fed into the second T-junction ($T_2$, 1 mm ID PEEK) of each reactor at a rate of 2.9 mL/min so as to prevent the backflow of liquids into the gas line. The gas flow distributor is able to precisely deliver gas into each reactor at the desired flow rate due to the careful calibration of the gas line as described in the experimental section. Coupled with the negligibly low downstream pressure drop in each reactor line compared with that in the flow distributor, the gas flow rate measured during the calibration is essentially identical to that infused into the final reactor network during its operation. Diisopropyl ether was subsequently fed into the first T-junction ($T_1$, 0.5 mm ID ETFE) of each reactor at a rate of 20 µL/min to form an organic-gas biphasic flow to pre-wet the walls of the reactors with the continuous organic phase; the biphasic flow was allowed to wet the reactor walls for about 15 min. It is observed that if the reactor walls were not wetted with the organic phase prior to the start of the full triphasic flow, the system would enter a cyclic start-stop mode of operation resulting from periodic pressure buildup within the reactor, as observed in our previous work, and the reactor network would take a much longer time to reach steady state (~2 h longer). Finally, water was fed into the first T-junction ($T_1$) of each reactor at a rate of 40 µL/min to form an organic-aqueous segmented flow in a 10 cm long 1 mm ID PTFE tube that connected $T_1$ to $T_2$. The biphasic segmented flow in each parallel reactor unit then formed a triphasic flow with the injected nitrogen gas at the $T_2$ prior to flow into a 30 m long 1 mm ID coiled PTFE tube. The reactor coils were stacked, and the outlet of each of the eight reactors was then reconnected by means of a network of T-junctions to form a single outlet stream (FIG. 1(b)). A photograph of the assembled reactor system is provided in FIG. 6.

Figure 7:
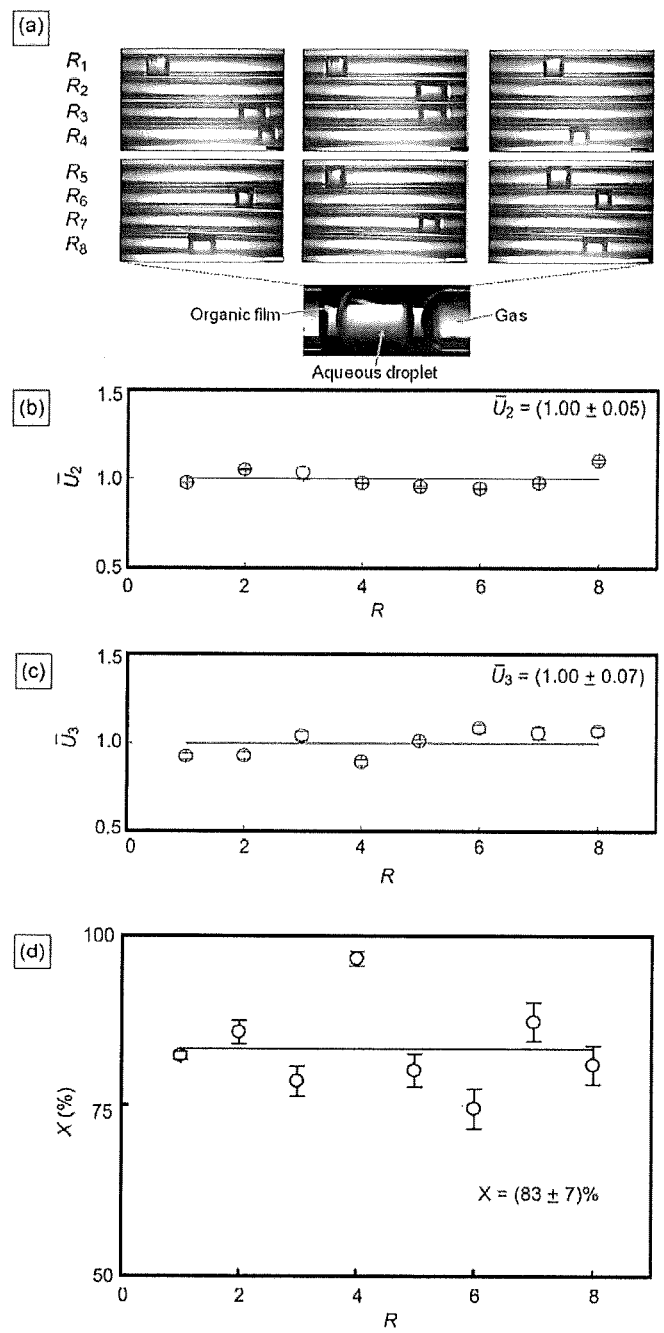

High-speed stereomicroscopic imaging (Basler piA640-210gm) at 50-200 frames per second (fps) was used to visualize the flow in each of the eight reactor lines, to assess flow uniformity and stability (FIG. 7(a)). Images of the biphasic and triphasic flow were recorded using high speed camera at 25 and 150 fps respectively. The flow speed was measured as the average time for an aqueous droplet or biphasic slug to travel a distance of 5.2 mm and 8.8 mm respectively within the field of view. Digital image analysis indicated that the flow speeds of the biphasic and triphasic flows in the eight parallel lines were within 5% and 7% deviation from each other (FIG. 7(b)-(c)). In addition, the triphasic flow morphology observed was similar to that of a single triphasic reactor designed in our previous work,[8, 9] highlighting the robustness of our parallelized system. Finally, in shutting down the reactor network, air was pumped through both the organic and the aqueous lines by means of a peristaltic pump, so as to remove the residual liquid in the system, while the flow of nitrogen gas was continued to facilitate the drying of the interior of the reactors. Once all the lines were free of liquid, the flow of air and nitrogen was halted.

7. Nanoparticle Catalyzed Hydrogenations with Continuous Online Catalyst Recycling Upon establishing the stability of the reactor network, the hydrogenation of nitrobenzene catalyzed by platinum nanoparticles (PtNPs) was carried out under near ambient conditions in two different modes: (i) without catalyst recycle, in which the variation in reactor performance across the eight parallel reactors in the network was examined, and (ii) with continuous catalyst recycle, in which the robustness of system operation over an extended run was examined. Both reactor modes leverage the highly intensified mass transfer in the triphasic flow regime, which allows gas-liquid reactions such as hydrogenation to be carried out under near ambient conditions, with orders of magnitude reduction in reaction time compared to their equivalent batch counterparts. For the first mode of operation, multiple samples were collected over the course of a few hours from the outlet of each reactor operating in parallel, and the substrate conversion (83±7%) in the system was found to be fairly consistent across each of the parallel reactors (FIG. 7(d)).

Figure 8:
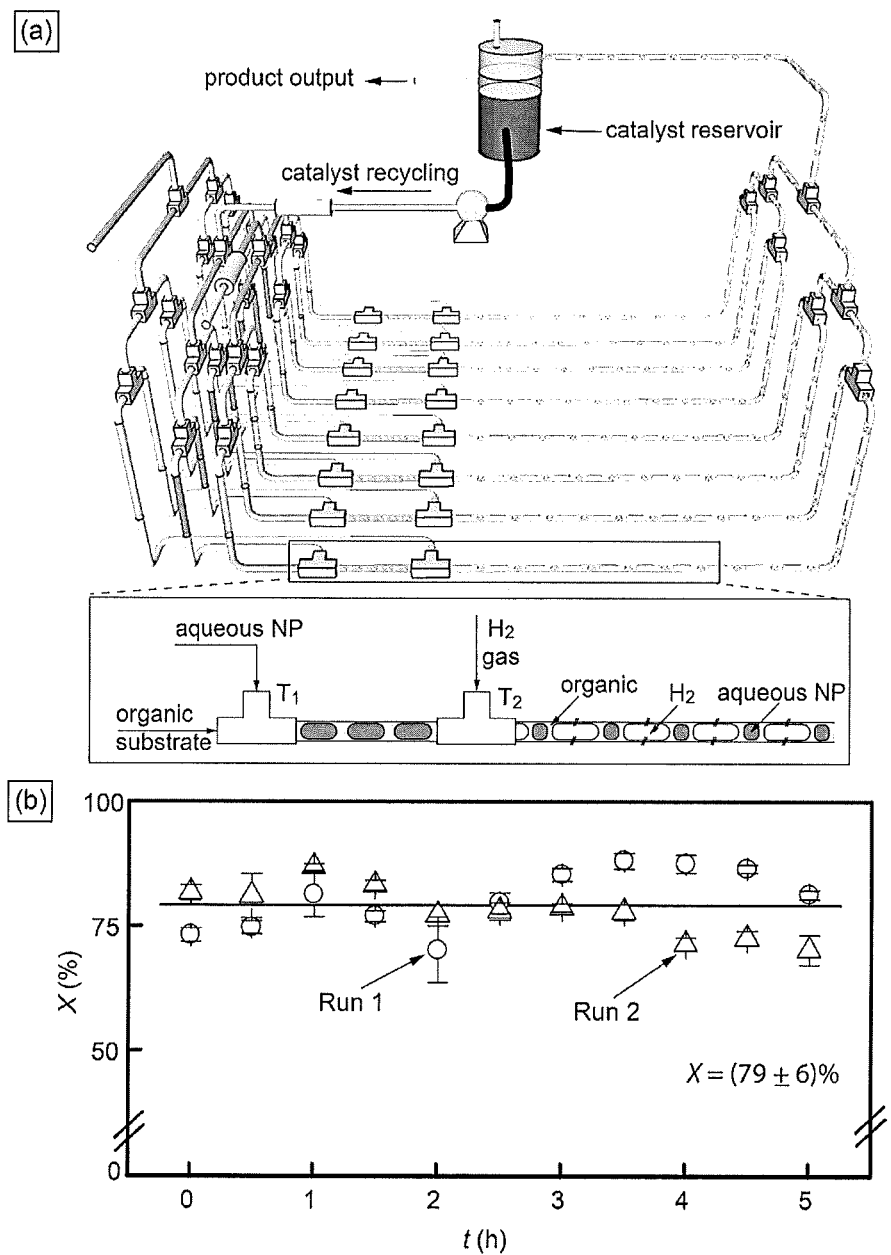
FIG. 8. (a) Schematic of triphasic flow reactor system for continuous catalyst recycling in the PtNP-catalyzed hydrogenation of nitrobenzene. Inset illustrates the formation of triphasic flow in each reactor. (b) Comparison of nitrobenzene conversion in the parallelized reactor system over the course of 5 hours for two separate experimental runs, highlighting the consistency in the output of the parallelized network.

Our reactor leverages a triphasic scheme to effectively compartmentalize the precious metal-based catalyst (nanoparticle or homogeneous) in an immiscible fluid phase to facilitate the easy separation of catalyst for subsequent recycling. Therefore, finally, we demonstrate continuous catalyst recycling for the same hydrogenation reaction. The setup for continuous catalyst recycling was almost identical to that without catalyst recycling, with the exception that the PtNP feed was withdrawn from the collection flask used to collect the effluent from the outlet of the reactor system. Approximately 60 mL of a 0.5 mM PtNP solution was first introduced into the collection flask during the startup of the reactor system. 100 mM nitrobenzene in diisopropyl ether, 0.5 mM aqueous PtNP solution and hydrogen gas were infused into each millireactor in the parallelized system at a rate of 20 μL/min, 40 μL/min and 2.9 mL/min respectively. The system was allowed to reach steady state for ~3 hours, during which samples from the outlet were continuously monitored via gas chromatography. Upon reaching steady state where nitrobenzene conversion remained approximately constant over time, the catalyst reservoir was topped up to ~50 mL and the biphasic effluent from the outlet of the reactor system was directed into the catalyst reservoir. The lower aqueous PtNP phase in the reservoir was agitated mildly at ~60 rpm to ensure homogeneity within the aqueous phase while avoiding emulsification of the aqueous-organic mixture in the flask. Samples from the outlet of the millireactor system were collected at 30 min intervals over a span of 5 hours, and were analyzed by means of gas chromatography. The reactor startup and shutdown procedures for continuous catalyst recycling were identical to the one described for the setup without catalyst recycling. The recycling experiment was done in duplicate, and the nitrobenzene conversion for both experimental runs was found to be 79±6% (FIG. 8). The PtNPs were able to provide sustained catalytic activity during the continuous recycling without significant variation in substrate conversion.

EXAMPLE 2

1. One-to-Many Parallelization of Millireactors with Inline Hydraulic Dampers for High Throughput Production The use of micro/millireactors as a platform for multiphase organic syntheses offers numerous advantages over its stirred-batch counterparts, such as accelerated heat and mass transport, enhanced operational safety and greater control over delicate reaction parameters. However, the micro/millireactors are known for their small volumetric throughput, ranging from μL/min to mL/min. Consequently, the use of micro/millireactor in an industrial-scale production will typically require a scaling-up in which the size of a reactor is increased, and/or a scaling-out (or numbering-up) concept in which multiple reactors operate in parallel simultaneously.

An alternative to increasing the throughput of micro/millireactors, multiple reactors can be designed to operate in parallel, a concept known as numbering-up or scaling out. In such systems, rather than having dedicated feed streams for each flow reactor, it is often more convenient for a single stream to be split into n streams for n number of reactors. However, the one-to-n splitting of fluid streams requires careful engineering design in order to ensure the even distribution of fluids into each of the reactors operating in parallel. It was previously demonstrated that the even distribution of fluids can be achieved via the incorporation of barrier-based channels into each parallel stream prior to entry into each reactor. This concept was then applied for the hydrogenation of phenylacetylene catalyzed by homogeneous rhodium catalyst.

In the infusion of feedstock into the micro/millireactors, syringe pumps are often the preferred mode of infusion for low throughput single reactors. While flow rate pulsations are absent in the use of syringe pumps, they are inherent in pumps such as peristaltic pumps and high pressure pumps which draw feedstock from a reservoir. Though the challenge of even fluid distribution in parallelized reactor systems can be addressed via the use of barrier-based channels, the issue of flow rate pulsations introduced by peristaltic pumps remain inherent in the absence of a proper damping system. For single phase micro/millireactors, the effects of flow rate pulsations may not have significant effects on the stability of the reactors. For multiphase reactors such as biphasic and triphasic micro/millireactors, the presence of flow rate pulsations may result in reactor instability given that the flow regime is highly dependent on the flow conditions such as the relative flow rates of the various feed. Flow rate pulsations introduced by pumps can be minimized via the incorporation of an inline hydraulic damper designed herein. While the challenges of even fluid distribution and flow rate pulsations can be addressed separately, the integration of both solutions into a single numbered-up micro/millireactor system requires careful engineering design to ensure an even distribution of feed into each flow reactor occurs at a constant, stable flow rate. The designed solution is then applied to a model parallelized triphasic millireactor system involving one gas feed and two liquid feed streams. The involvement of multiple fluid phases thus requires very stringent design conditions to ensure the stability of the parallelized reactor system. In this work, the challenges of both even fluid distribution as well as the diminishing of flow rate pulsations in numbering up micro/millireactors will be addressed via the incorporation of both barrier-based channels and inline hydraulic dampers in a carefully designed system. A simplified design for a one-to-eight parallelized micro/millireactor systems is demonstrated in the hydrogenation of nitrobenzene, a model pharmaceutical substrate, catalyzed by platinum nanoparticles (PtNPs). Finally, the numbered-up millireactor system is then used to demonstrate the continuous online recycling of the PtNP catalyst in the hydrogenation reaction.

2. Design of Damper

Figure 9:
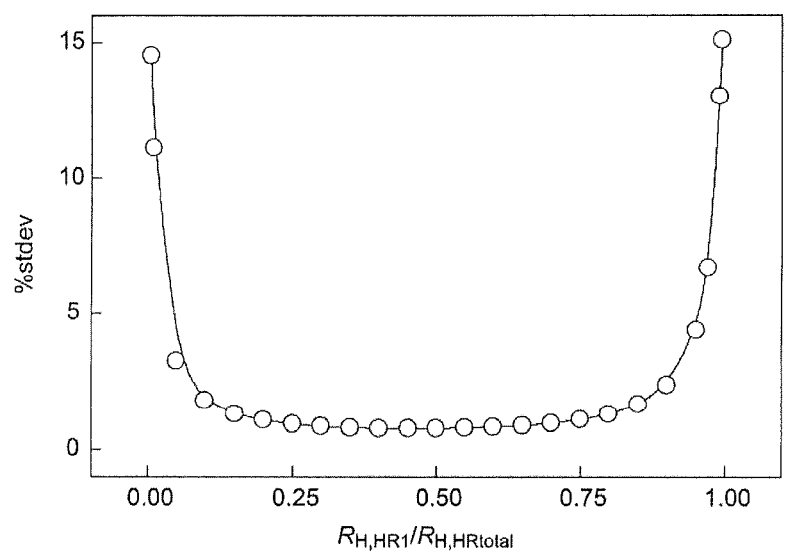
FIG. 9. Plot of the extent of flow rate pulsations against the ratio of hydraulic resistance of a network of tubes (see FIG. 4) before and after the elastic damper. $R_H$ refers to the hydraulic resistance. $R_{H,HR1}$ refers the hydraulic resistance of the network of tubes before the elastic damper, while $R_{H,HRtotal}$ refers to the total hydraulic resistance of the network of tubes before and after the elastic damper.
Figure 21:
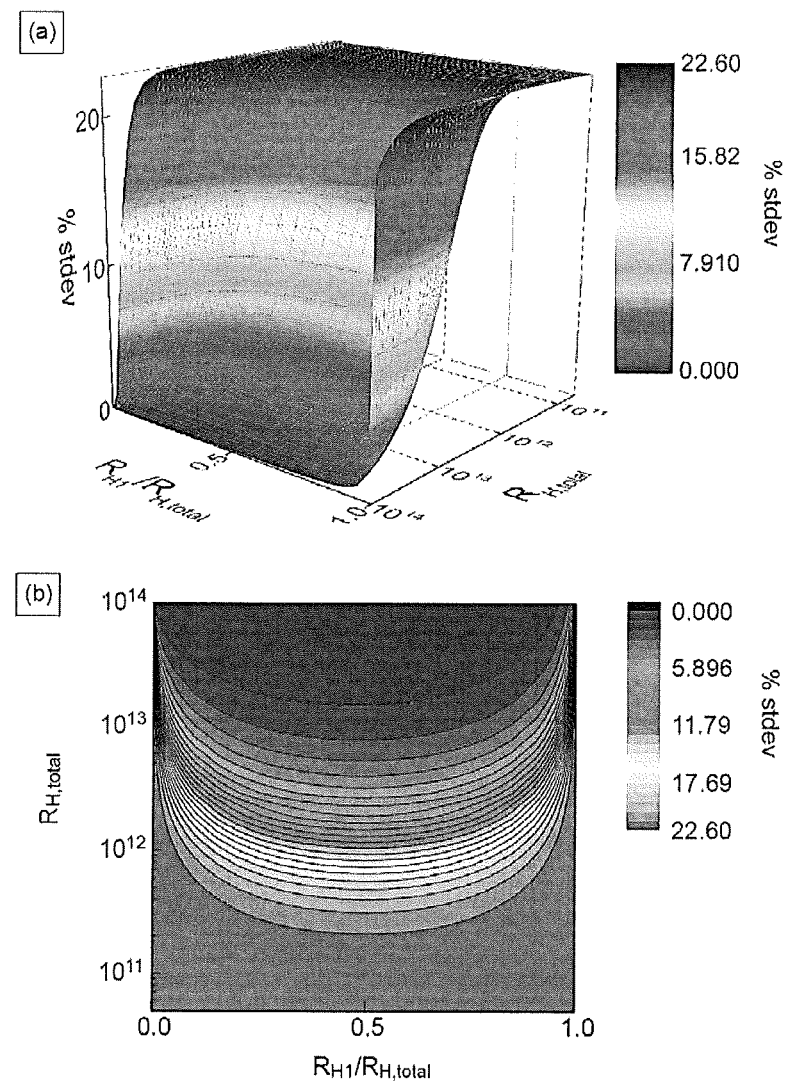
FIG. 21. (a) Surface and (b) contour plot of the extent of pulsations against the ratio $R_{H,1}/R_{H,total}$ and the total hydraulic resistance $R_{H,total}$ in a PEEK-Silicone-PEEK tube configuration.
Figure 22:
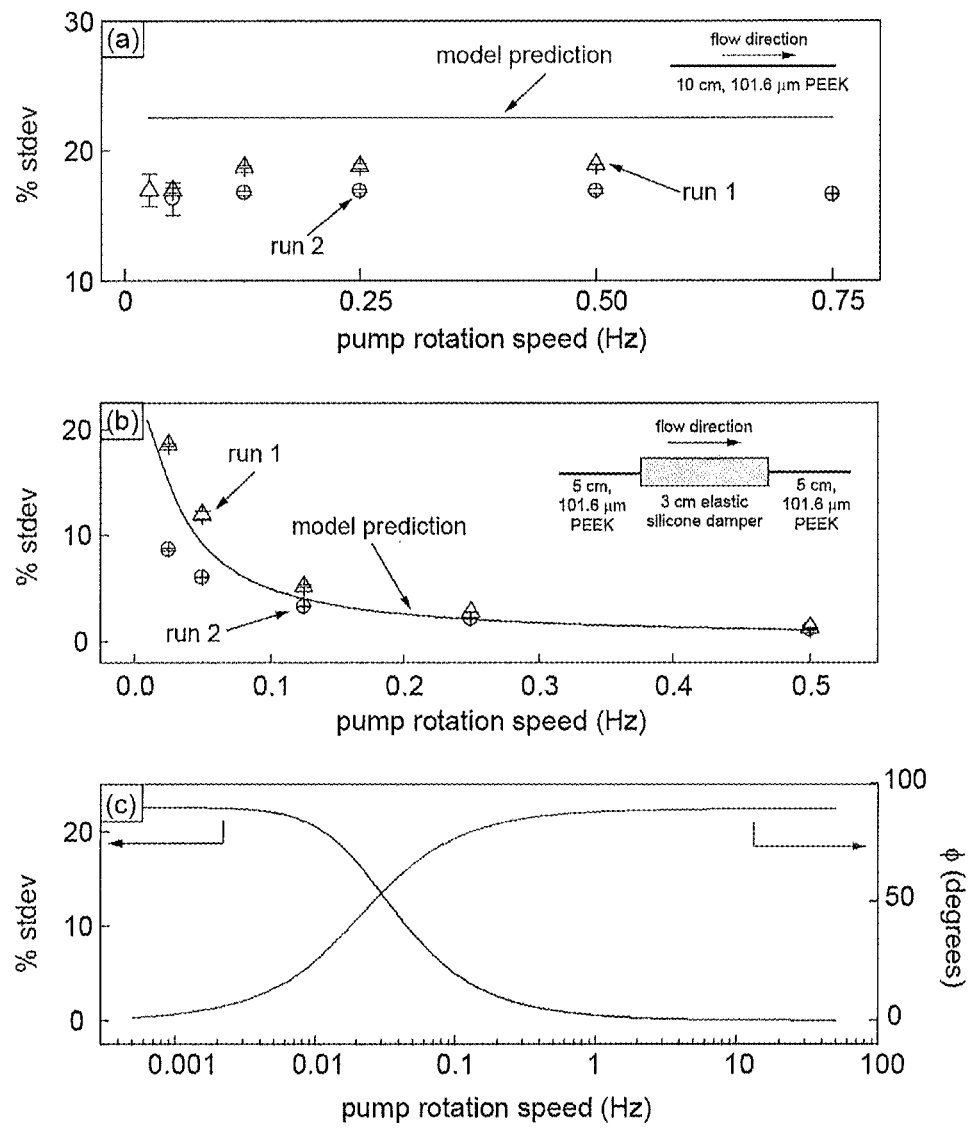
FIG. 22. Comparison of the extent of flow rate fluctuations at different pump speeds for two experimental runs for (a) a 10 cm long 101.6 μm PEEK tube and (b) an inline hydraulic damper with a 3 cm long silicone tube sandwiched between two 5 cm long 101.6 μm PEEK tubes. Both the experimentally observed trends and model predictions show (a) an independence between flow rate pulsations and pump speeds and (b) a decline in flow rate pulsations at higher pump speeds. (c) Plotted is the mathematically predicted trend of phase shift ϕ between the change in inner radius of the silicone tube with that of pressure pulsations from the pump as well as the corresponding flow rate pulsations at different pumps speeds.

In a previous design of an inline hydraulic damper, it is recommended for an elastic damper tube to be sandwiched between two tubes with significant hydraulic resistance. However in this study, it is discovered that such requirement can be generalized. In a mathematical model which incorporates the effect of fluid structure interaction between the flowing fluid within the damper and the elastic damper material, the effectiveness of damping provided by the elastic tube can be calculated. Using this model, the hydraulic resistance of tubes before and after the damper is varied, and it is found that the optimum damping provided by the elastic damper occurs when the ratio of hydraulic resistances of the components (i.e. either a single tube or a network of tubes) is equal before and after the damper tube (FIG. 9). In addition, the higher the total resistance of the hydraulic components in the circuit, the better is the damping effect (FIG. 21), and the operation of the hydraulic damper at a higher pulse frequency provides a better damping for an elastic damper compared to one operated at a lower pulse frequency (FIG. 22). Consequently, for a network of tubes with pulsatile flow, a single damper can be installed in a manner illustrated in FIG. 12. Following this, a network of tubes illustrated in FIG. 10b is assembled, and the flow instantaneous flow rate in a network of tubes is measured and compared to a control case wherein no damper is installed (FIG. 11).

3. Design of Fluid Distributor

Figure 13:
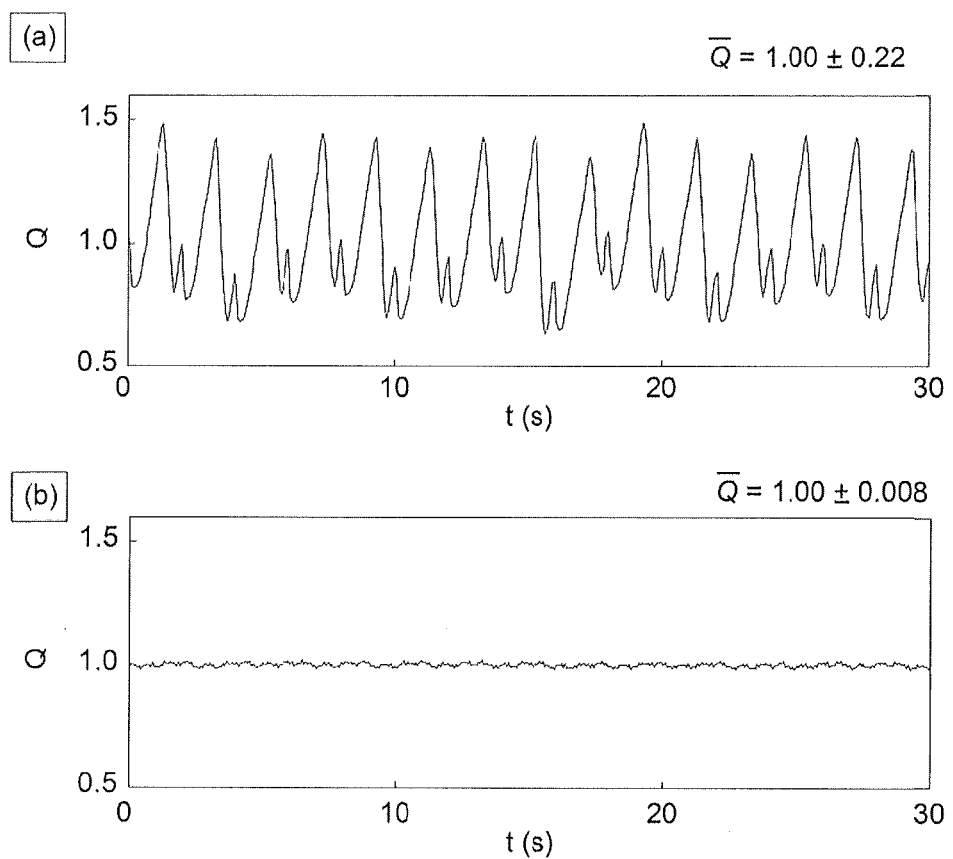
FIG. 13. Comparison of normalized instantaneous flow rate Q for pulsatile flow in a hydraulic circuit with (a) no damper and (b) with a master damper.

In contrast to having a dedicated inline hydraulic damper for each of the eight parallel lines (see FIG. 13), the liquid distributor (LD) herein uses the concept of a master damper placed prior to the distribution of liquid into eight parallel streams (FIG. 10). It was determined that a good hydraulic damper configuration involves the placement of an elastic tube of a wide diameter (e.g. L/S 25 viton or silicone tube) between two tubes with a significantly higher hydraulic resistance than the elastic tube. However, here, it is discovered that for as long as an elastic damper tube is sandwiched between two hydraulic components with significantly high hydraulic resistance, the effect of the hydraulic damping remains effective. Here, in the design of LD for the organic line, a 40 cm long 101.6 μm ID PEEK tube (i.e. a tube with high hydraulic resistance) is fitted to one end of the 8 cm long L/S 25 elastic viton tube which functions as the damper. The other end of the viton tube is then connected to the network of T-junctions consisting of eight parallel 5 cm long 63.5 μm ID PEEK tubes—the combination of these eight tubes in a network provides significant hydraulic resistance that the elastic damper requires for an effective reduction in pressure pulses introduced by the peristaltic pump. In other words, the network of eight PEEK tubes as well as the 40 cm long PEEK tubes at each end of the elastic viton tube provide the hydraulic resistance required for an effective damping of flow pulsations. In contrast to the setup in FIG. 10 where the entire inline hydraulic damper serve as the barrier-based tubes, for the LD developed herein, only the eight parallel PEEK tubes serve as the barrier-based tubes for the even distribution of fluids. Using diisopropyl ether as the organic solvent, a pump gauge pressure of 1.33 atm is provided for the delivery of the solvent at a rate of 20 μL/min in each of the eight lines. The final design of the LD for the organic line is thus given in 2a.

The LD for the aqueous stream is similarly designed, with a pump gauge pressure of 1.31 atm, and its final configuration is given in FIG. 2b. The flow rate of water through each of the eight parallel lines is 40 μL/min.

4. Design of Millireactor System

In the design of the triphasic millireactor system, a one-to-eight distributor for gas line (identical to the one given in the previous design), LD for both organic and aqueous lines (designed herein) are assembled to give eight parallel triphasic millireactors. Diisopropyl ether and water are infused into the first T-junction (0.5 mm ID ETFE) of each millireactor at a rate of 20 μL/min and 40 μL/min respectively to form an organic-aqueous droplet train in a 10 cm long 1 mm ID PTFE tube. The train of droplets is then fed into the second T-junction (1 mm ID PEEK) where nitrogen gas at near ambient condition is introduced into each millireactor. The resulting triphasic train is then directed into a 30 m long 1 mm ID PTFE tube. The outlet of each of the eight millireactors is then reconnected by means of a network of T-junctions to form a single outlet stream. A schematic of the millireactor system is given in FIG. 8. High speed microscopic imaging (Basler piA640-210gm) at 50 to 200 fps is used to observe the flow behavior of both the biphasic and triphasic flow in each of the eight millireactors.

Following the flow study, the hydrogenation of nitrobenzene catalyzed by PtNPs is carried out in the millireactor system. 100 mM of nitrobenzene in diisopropyl ether, 0.5 mM PtNPs and hydrogen gas are infused into each millireactor at a rate of 20 μL/min, 40 μL/min and 2.89 mL/min respectively at near ambient conditions. The residence time of the triphasic flow in each millireactor is approximately 7.75 min. Samples are collected periodically at the outlet of each millireactor over the course of a few hours, and the composition of the top organic product phase is analyzed via gas chromatography. Samples are collected periodically at the outlet of each millireactor over the course of approximately five hours, and the composition of the top organic product phase is analyzed via gas chromatography (Shimadzu 2010Plus). From the percentage composition of the product aniline to that of aniline and nitrobenzene, the percentage conversion of nitrobenzene to aniline can be determined. Once the millireactor system reaches steady state after ~3 h, i.e. the conversion of nitrobenzene in each reactor is approximately constant, the values of nitrobenzene conversion are noted down for analysis.

In the recycling of catalyst in the numbered-up triphasic millireactor system, the setup is almost identical to that described earlier, with the exception that the PtNP feed is withdrawn from the collection flask which is used to collect the product from the outlet of the millireactor system (FIG. 8). ~60 mL of 0.5 mM PtNPs is first introduced into the collection flask during the startup of the millireactor system. 100 mM nitrobenzene in diisopropyl ether, 0.5 mM PtNPs and hydrogen gas are infused into each millireactor at a rate of 20 μL/min, 40 μL/min and 2.89 mL/min respectively. The system is allowed to reach steady state for a ~3 h, during which samples from the outlet of the millireactor system are continuously monitored via periodic sample analysis by means of gas chromatography. Upon reaching steady state (i.e. substrate conversion remains approximately constant over time), the reservoir of PtNPs is topped up to ~50 mL and the product from outlet of the millireactor system is directed into the same round bottom flask in which the reservoir of PtNPs is held. The organic and the aqueous phase undergoes phase separation in the collection flask, and the aqueous phase containing the PtNPs undergoes mild agitation with a stir speed of 60 rpm to ensure homogeneity within the aqueous phase while avoiding emulsification of the organic-aqueous mixture in the collection flask. Samples from the outlet of the millireactor system are collected at 30 min interval over a span of 5 h, and are analyzed by means of gas chromatography. All experiments mentioned herein are done in duplicate.

5. Results

Figure 14:
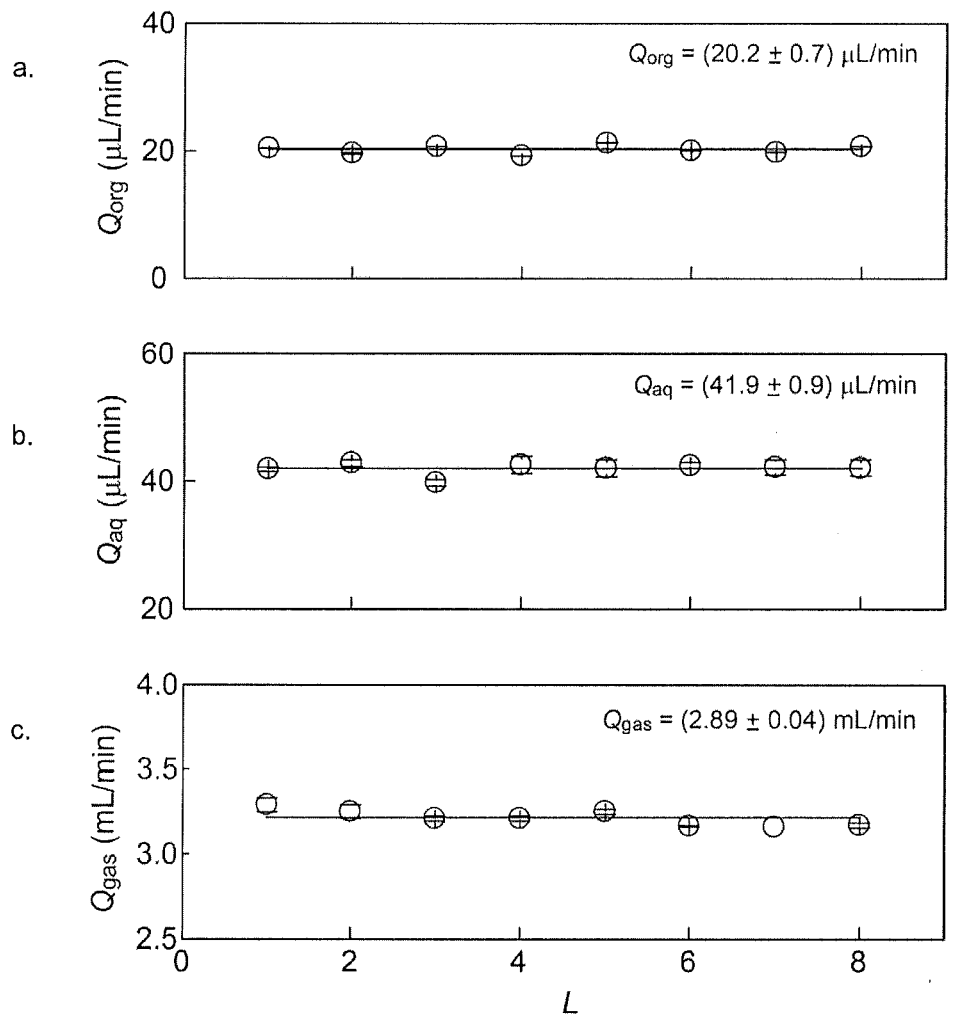
FIG. 14. Comparison of fluid flow rate Q across the eight parallel lines (L) in the (a) organic (b) aqueous and (c) gas flow distributors highlighting the even distribution of fluids in the respective flow distributor.
Figure 15:
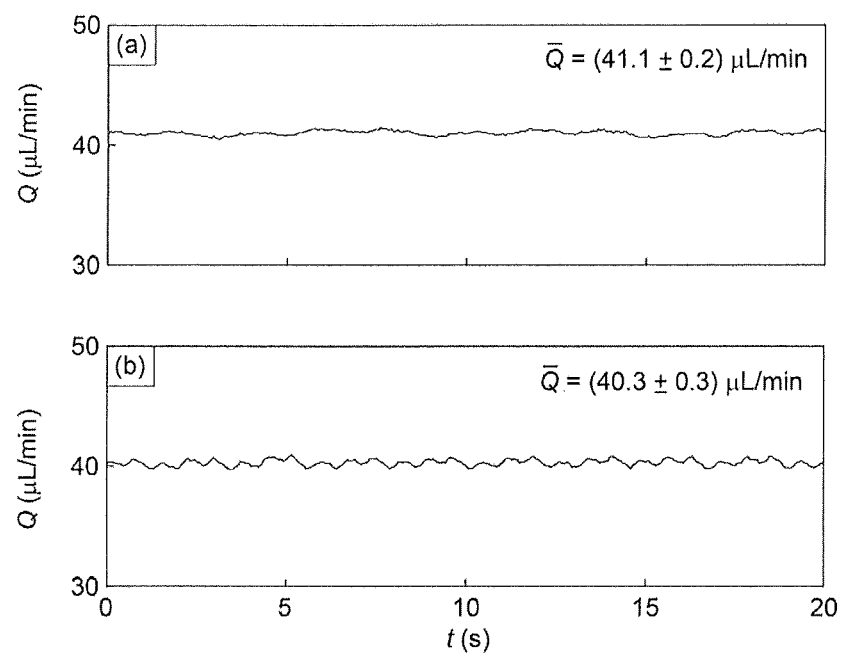
FIG. 15. Comparison of variation in instantaneous flow rate Q in a single line for (a) a previously designed flow distributor with dedicated inline hydraulic damper [1] and (b) flow distributor 2 with a single master damper designed herein. The deviation from average flow rate for both types of flow distributors are small and negligible.

FIG. 14 shows the consistency of average fluid flow rate (measured experimentally) in each of the eight lines, highlighting the effectiveness of the designed fluid distributor. In comparing the damping effectiveness of the liquid distributor designed herein to that designed in a previous work, FIG. 15 shows a plot of instantaneous flow rate for each of the design. From FIG. 15, it is immediately apparent that despite the simplification from having one damper in each of the eight parallel lines to having only a single master damper for the entire liquid distributor, the flow pulsations after passing through the hydraulic damper remains low.

Figure 16:
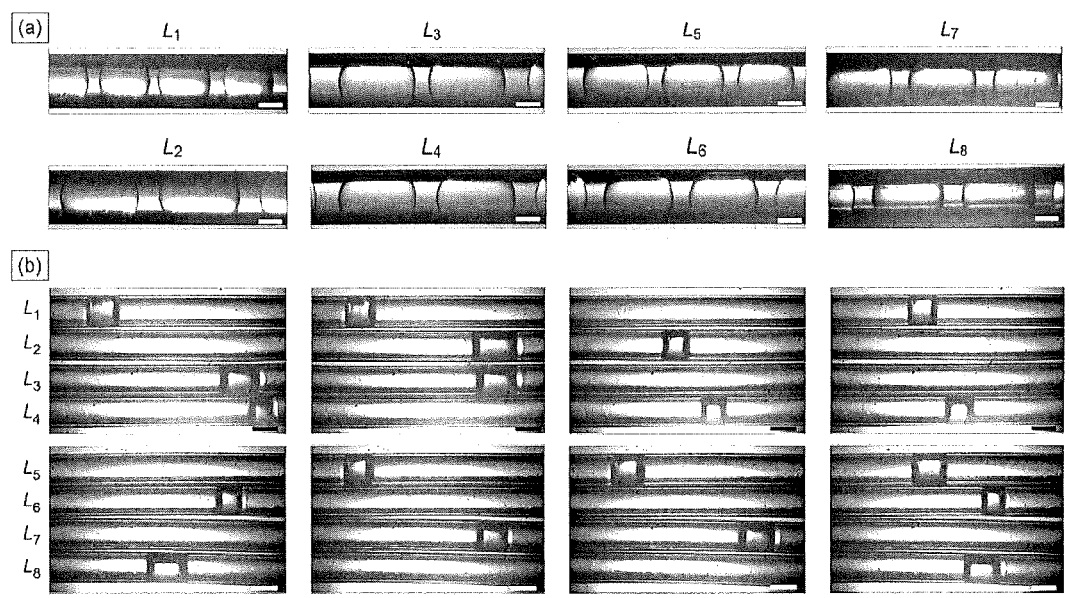
FIG. 16. (a) Stereomicroscopic images of organic-aqueous biphasic droplet train in the numbered-up millireactor system in lines $L_1$ to $L_8$. Each scale bar represents 0.5 mm. (b) Snapshots of triphasic flow in the eight parallel millireactors in lines $L_1$ to $L_8$. Each scale bar represents 1 mm.
Figure 17:
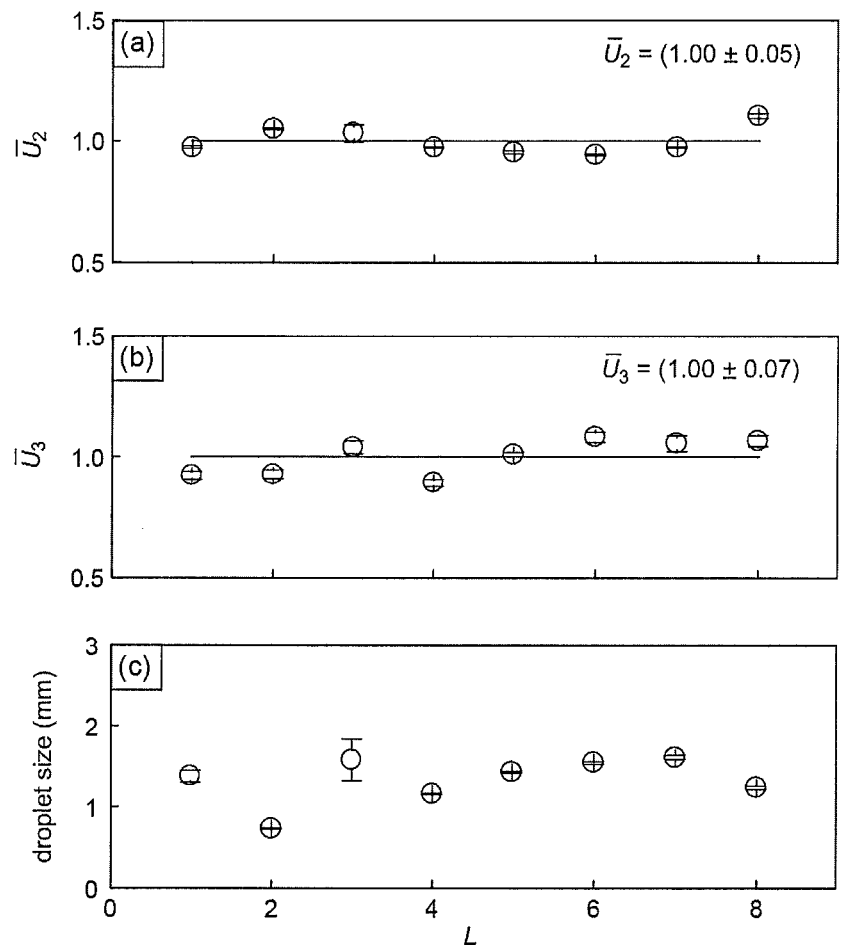
FIG. 17. Comparison of normalized multiphase flow speed U for (a) aqueous-organic biphasic flow and (b) gas-aqueous-organic triphasic flow in the eight parallel lines L. The variation in flow speed in both the biphasic and triphasic flows across the eight parallel lines are observed to be very small. (c) Plot of aqueous-organic biphasic droplet size across the eight parallel millireactors.

Following this, a flow study is conducted by flowing water, diisopropyl ether and nitrogen gas into the millireactor system. The biphasic and triphasic flow in the eight reactors are visualized by means of a high speed camera attached to a stereomicroscope (FIG. 16), and the standard deviation of the biphasic and triphasic flow speeds in all eight lines are found to be 5% and 7% respectively (FIGS. 17a and b), highlighting the narrow deviation in multiphase flows in the eight parallel lines.

Figure 18:
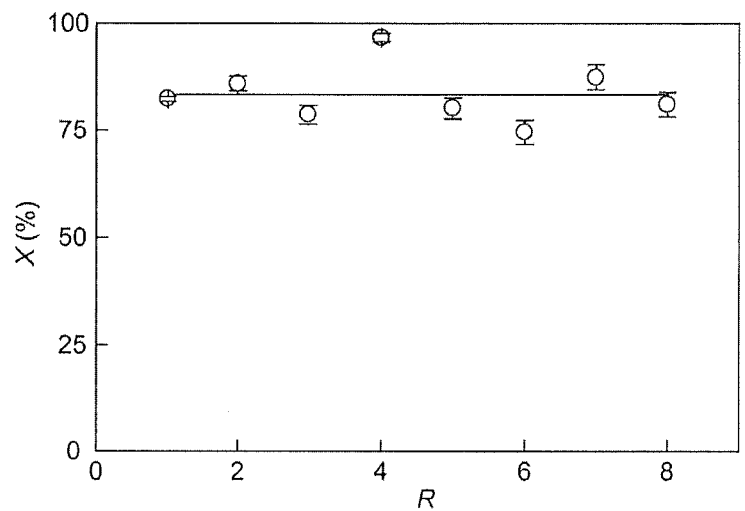
FIG. 18. Comparison of nitrobenzene conversion X across eight parallel millireactors R in the parallelized millireactor system, highlighting the consistency in substrate conversion in the parallelized system.
Figure 19:
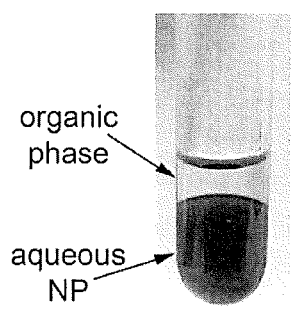
FIG. 19. Photograph of the reaction mixture collected at the outlet of the millireactor. The aqueous nanoparticle catalyst-carrying phase is immiscible with the organic product phase. The aqueous catalyst can therefore be easily separated from the reaction mixture for recycling.
Figure 20:
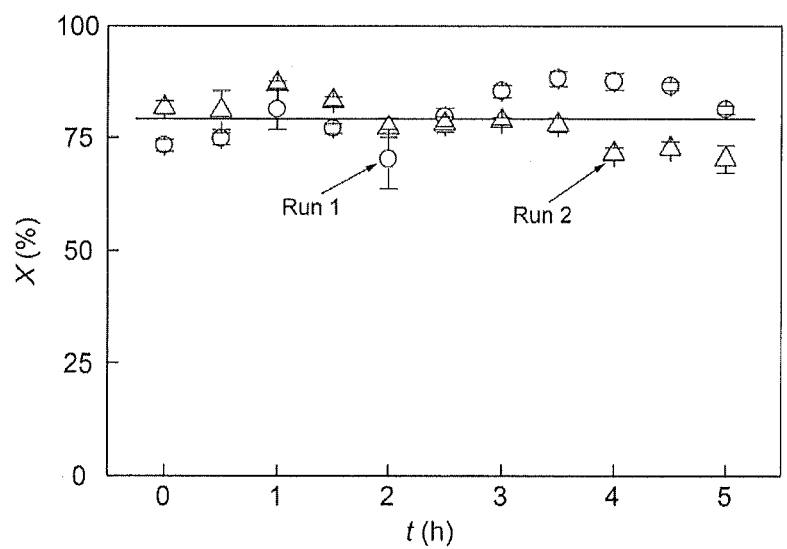
FIG. 20. Comparison of nitrobenzene conversion X across eight parallel millireactors R in the parallelized millireactor system for two separate experimental runs, highlighting the consistency in substrate conversion in the parallelized system.

Upon establishing the stability of the parallelized triphasic millireactor and its flow regime, the hydrogenation of nitrobenzene catalyzed by PtNPs is carried out in the parallelized millireactor system under near ambient conditions. With near identical reaction conditions of operation for both the current millireactor system and that designed previously, the substrate conversion for this designed millireactor system thus follows that of the previous design very closely, with the conversion of nitrobenzene herein being (83±6.7)% compared to (80±3.8)% in the previous design (FIG. 18).

In the demonstration of continuous catalyst recycling, the outlet of the eight millireactors are combined into a single stream for product collection in a round bottom flask, and the catalyst is continuously recycled over the span of 5 h. In the development of a single triphasic millireactor for catalytic hydrogenation, a triphasic scheme is used for the purpose of encapsulating the catalyst (nanoparticle or homogeneous) in an immiscible fluid phase to facilitate the easy separation of catalyst for subsequent recycling. Here, the properties of this design are exploited for continuous catalyst recycling.

100 mM nitrobenzene in diisopropyl ether is hydrogenated at near ambient conditions in eight parallel millireactors at a rate of 9.6 mL/h in the presence of 0.5 mM PtNPs dispersed in water flowing through the millireactor system at a rate of 19.2 mL/h. The outlet of the millireactor system is directed into a round bottom flask, where the unreacted hydrogen gas exits the flask through a tube inserted at the mouth of the flask, and the liquid phases undergo phase separation, with the lighter organic phase floating above the denser aqueous nanoparticle catalyst-carrying phase. A clear phase separation line can be seen, similar to that shown in FIG. 13. The bottom aqueous phase undergoes continuous mild agitation to ensure that the bottom catalyst-carrying phase is well-mixed without resulting in emulsification of the organic and the aqueous phase. The catalyst-carrying phase is then recycled and redirected back into the parallelized millireactor system in a continuous fashion by means of a peristaltic pump for subsequent hydrogenation reactions. With a catalyst reservoir of 50 mL, the operation of the millireactor system with continuous catalyst recycling implied an average catalyst recycling turnover of ~2 at the end of 5 h.

A sample of the product at the outlet of the millireactor system is collected at the outlet of the millireactor in 30 min intervals, and the conversion of nitrobenzene is determined by means of gas chromatography. The experiment is done in duplicate, using PtNP catalysts synthesized on two separate occasions to ensure repeatability. The conversion of nitrobenzene for both experimental runs is found to be X=(79.2±5.6)%.

From FIG. 14, it is observed that the PtNPs are able to provide sustained catalytic activity during the 5 h of continuous recycling.

In summary, while the parallelized millireactor system designed in this study is much simplified compared to that of a previous work, it is able to provide a similar performance as that of the previous design. The drastic simplification in the parallelized millireactor system enables multiple benefits, including lower dead volume, shorter reactor startup and shutdown time as well as greater ease of reactor maintenance.

EXAMPLE 3

It was previously demonstrated that the application of inline hydraulic dampers for the effective damping of flow rate pulsations in both single channel and multichannel fluid flow in millireactors. The inline hydraulic damper is a simple setup, consisting of an elastic tube sandwiched between two flow networks of significant hydraulic resistance. Here, we demonstrate the application of the inline hydraulic damper in providing autonomous disturbance regulation in a passive network as well as in reactor networks with significant pressure drop.

1. Autonomous Disturbance Regulation

Figure 23:
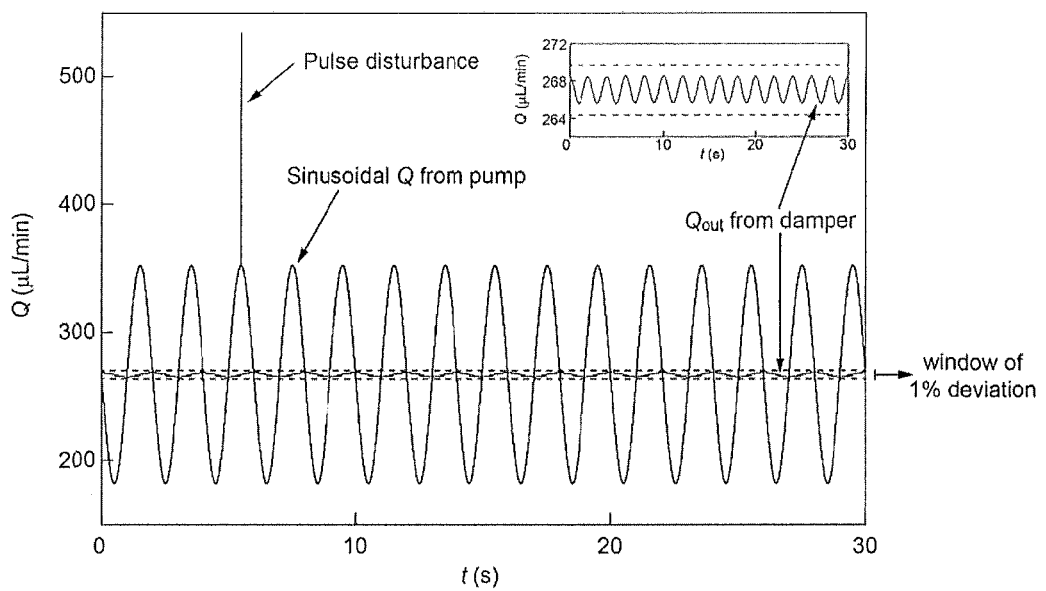
FIG. 23. Plot of instantaneous flow rate of water exiting an 8 cm long silicone damper when subjected to a 0.01 s pulse disturbance at t=5 s, highlighting the minimal change in exit flow rate measured despite the presence of disturbance. Inset focuses on the compliance of exit flow rate from the damper within a tolerance of 1% of the steady state flow rate.

The incorporation of an elastic damper tube within a flow network is not only able to damp out periodic pulsations introduced by pumps, but also provide passive, autonomous regulation of flow rates in the presence of temporal disturbances. Here, the effectiveness of an 8 cm long 4.76 mm ID silicone damper sandwiched between two networks of tubes, each with a hydraulic resistance of 1.91 Pa·s/m3, in providing autonomous regulation in the presence of temporal disturbances is studied using the mathematical model we have derived previously. FIG. 23 demonstrates the case when a pulse disturbance with an amplitude that is equal to the time-average steady state flow rate (267 µL/min) is introduced to the peak of the sinusoidal flow rate input for 0.01 s.

From FIG. 23 it is evident that despite the presence of a pulse disturbance, the elastic damper is able to provide autonomous regulation via the absorption of the sudden change in flow rate disturbances without resulting in any significant change in the flow rate exiting the damper. The flow rate exiting the damper thus remains within the window of 1% deviation from the steady state flow rate. In contrast, if no hydraulic damper is installed, any sudden change in flow rate infused into the system will be reflected as a change in flow rate that is equal in magnitude and duration downstream. Consequently, the plot of instantaneous flow rate measured in a system without a damper would be identical.

If, however, the damper is not able to absorb the pulse disturbance, an increase in flow rate will be observed at the outlet of the damper from the time of the spike, followed by a steady decay towards the steady state oscillatory behavior.

Figure 24:
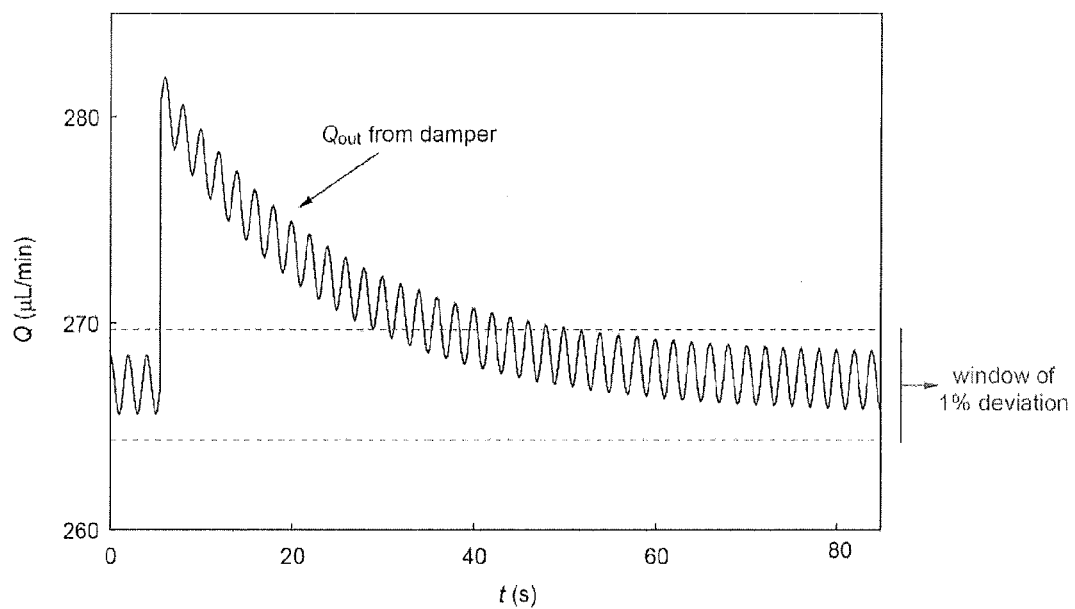
FIG. 24. Flow behavior of water exiting an 8 cm long silicone damper when subjected to a 0.01 s pulse disturbance with a magnitude of a hundred times the steady state flow rate at t=5 s. A deviation of flow rate from the steady state flow rate is observed when the damper is unable to adequately absorb the pulse disturbance.

In a demonstration case presented in FIG. 24, a sudden pulse disturbance with an amplitude of 100 times the amplitude of the steady state flow rate is introduced into the oscillatory flow rate infused into an 8 cm long 4.76 mm ID silicone damper at t=5 s for a duration of 0.01 s. At the instant when the pulse disturbance is introduced, a sudden increase in the oscillatory flow rate is observed. Despite the presence of the sudden increase in flow rate observed at the outlet of the damper, the amplitude spike is only 0.056 times the steady state flow rate, a significant diminishment of the amplitude of 100 times pulse input. The much smaller spike in fluid flow rate followed by a steady decline is attributed to the ability of the elastic damper to expand and absorb the sudden surge in fluid influx so that the increase in fluid uptake is not immediately released as fluid outflow from the damper by the same extent. The sudden surge in fluid uptake results in an increase in radial pressure within the elastic tube above the steady state oscillatory values. Consequently, the highest fluid outflow from the damper is observed at the instant when the radial pressure is the highest (i.e. approximately the time when the pulse disturbance is introduced), and the remaining excess fluid is gradually released over time as the radial pressure within the tube decays to its steady state oscillatory value.

Figure 25:
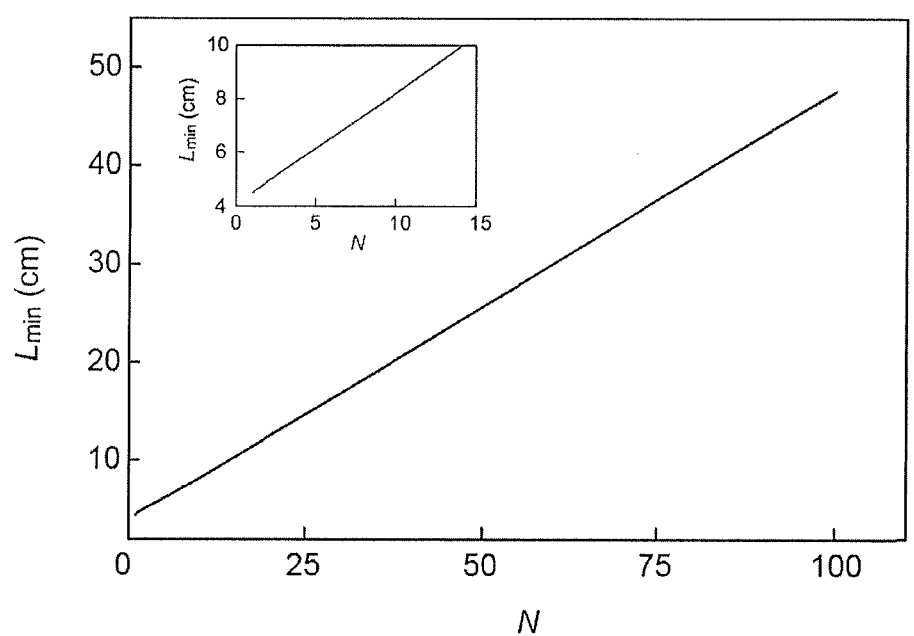
FIG. 25. Plot of the minimum length, $L_{min}$, of silicone damper required to maintain the fluid flow rate from the outlet of the damper to within a deviation of 1% of the steady state flow rate with a pulse disturbance of amplitude N times the amplitude of the steady state flow rate is introduced into the system.

A minimum damper tube length ($L_{min}$) is then calculated to maintain the fluid outflow from the damper to within a deviation of 1% from the steady state flow rate when a 0.01 s pulse disturbance of amplitude N is introduced into the flow (FIG. 25). Here, N represents the ratio of the amplitude of disturbance to the steady state flow rate (267 μL/min). The results calculated from the model shows that for a short damper of a mere 10 cm in length (internal volume of 1.78 mL) is able to absorb a disturbance of N>10, highlighting the excellent performance of elastic dampers in providing autonomous regulation.

Figure 26:
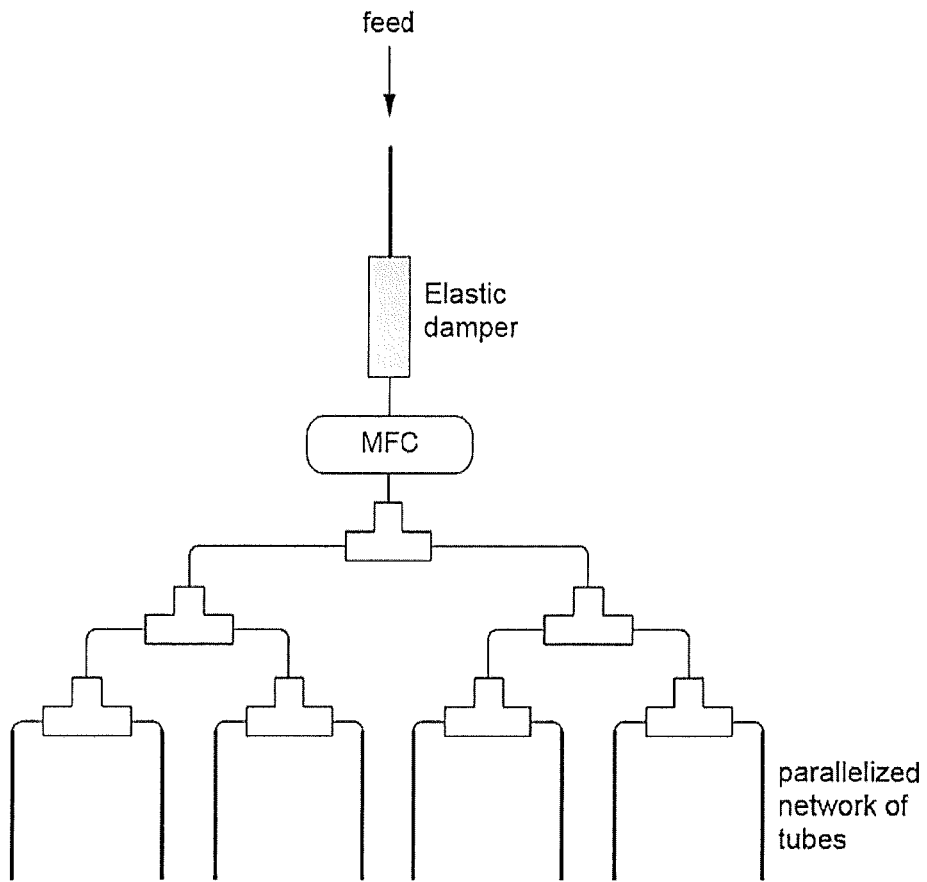
FIG. 26. Schematic illustrating the integration of an active controller such as a mass flow controller (MFC) with a passive controller (an elastic damper) in a parallelized system.

In an actual production line, the presence of passive, autonomous regulation is crucial in the design of a robust flow network. While active controllers such as mass flow controllers (MFC) are able to provide active regulation in simple flow circuits, the amount of regulation that active digital controllers can provide in a highly branched flow network with time-varying signals is limited. As such, it is necessary to incorporate designs that are able to provide passive and autonomous regulation in such complex systems. In an actual industrial scale production, the integration of active controllers with passive controllers is essential for the smooth operation of a massively parallelized reactor system. FIG. 26 illustrates an example of an integration of the two controllers in a parallelized flow circuit. The incoming oscillatory fluid feed from the pump, along with any disturbances, is first damped out by means of an elastic damper which provides the passive regulation as well as the smoothening of the pulsations. Thereafter, the pulse-free flow is directed into an active controller such as an MFC which then ensures that the flow rate is in compliance with the setpoint, prior to the distribution of the fluid flow into the parallelized network. In integrating the use of both active and passive controllers, flow within a massively parallelized network of flows is thus more stable and robust.

Figure 27:
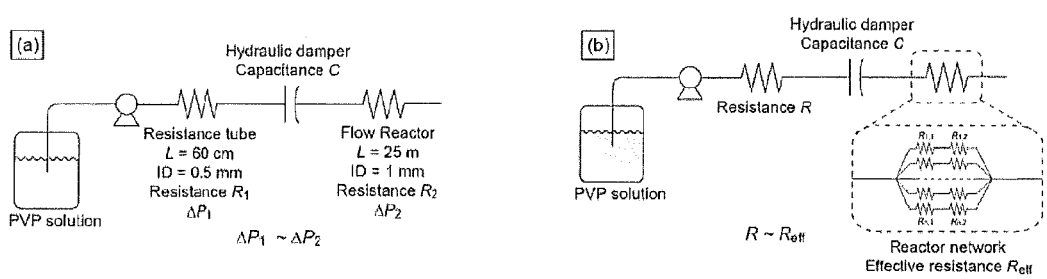
FIGS. 27 (a) and (b). Schematic of a massively parallelized flow network for large-scale, high throughput production.

2. Application of Inline Hydraulic Damper for Reactor Network with Significant Pressure Drop In the integration of an inline hydraulic damper within a flow distributor involving a network of tubes, the flow distributor has been applied to a parallelized triphasic millireactor system wherein the hydraulic resistance and hence pressure drop across the reactor system is small ($\Delta P \sim 0.015$ atm) compared to that across the flow distributor ($\Delta P \sim 1.3$ atm). The integration of damper into a flow distributor can too be applied should significant hydraulic resistance or pressure drop be present in each of the reactor operating in parallel be significant. For instance, in the infusion of a viscous solution (e.g. aqueous polyvinylpyrrolidone (PVP) solution) by a peristaltic pump (or any pump which gives periodic, time-varying flow rate) into a 25 m long, 1 mm inner diameter (ID) PTFE millireactor (pressure drop $\Delta P$ across millireactor is ~2 atm), the following setup illustrated in FIG. 27a can be designed to incorporate the use of the designed hydraulic damper into the reactor system. Here, an elastic damper tube such as a silicone tube or a tygon tube is sandwiched between a 60 cm long, 0.5 mm ID tube and a 25 m long, 1 mm ID flow reactor, both of which are of similar hydraulic resistances, and confer approximately a pressure drop of 2 atm across each of the mentioned hydraulic components. As consistent with the original design of an effective hydraulic damper wherein an elastic damper tube is sandwiched between two tubes with significant and approximately equal hydraulic resistances, the elastic damper tube herein is sandwiched between a tube and a reactor, both of which has approximately equal hydraulic resistances. A similar extension can thus be made for a reactor system with an effective hydraulic resistance $R_{eff}$, where $R_{eff}$ is the effective resistance of any channels or tubing designed to confer a specified amount of hydraulic resistance to the circuit, and the resistance of the reactors operating in parallel, to achieve effective damping (FIG. 27b).

Figure 28:
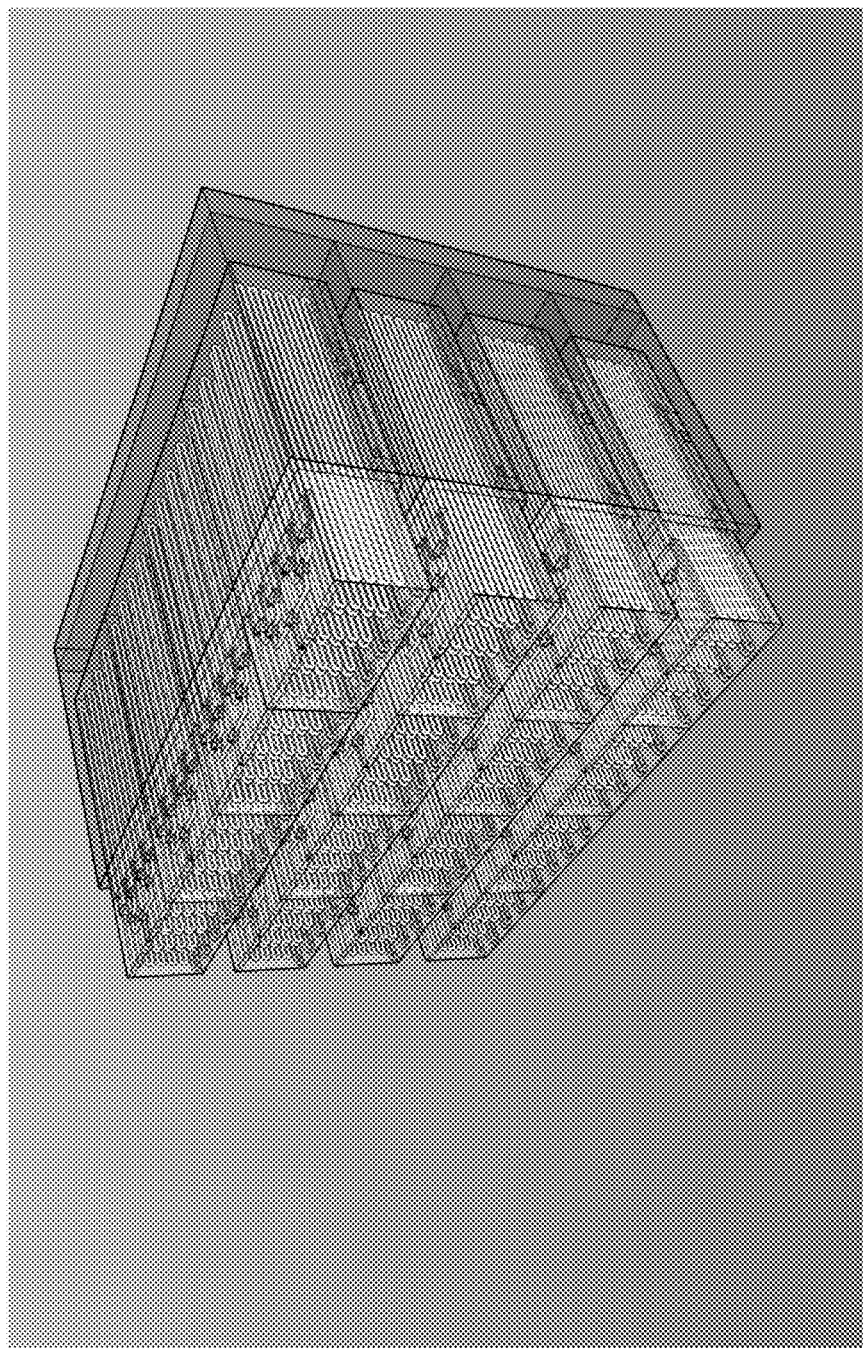
FIG. 28. Schematic of a massively parallelized flow network.

The designed flow distributor with inline hydraulic damper(s) can be further incorporated into a massively parallelized flow network such as one shown in FIG. 28. Here, each unit consists of a set of parallelized flow network (e.g. a given number of millireactors), with its dedicated flow distributor and an inline hydraulic damper in each set. Each set of flow network is then assembled into a 'drawer'-like configuration which can operate either standalone, or be inserted into a larger network for higher throughput operations. In the event where there is a need to troubleshoot certain identified set(s) of flow network due to flow maldistribution, reactor fouling etc, the identified set can be removed from the large manifold to be either replaced by another functional set, or be left empty, since automated flow rate adjustments will be ensured upon the removal of the dysfunctional set by a mass flow controller or any appropriate active controller hooked up in the main system.

When incorporated into a flow network or a flow circuit, the designed inline hydraulic damper herein is not only able to damp out flow rate pulsations, but also provide autonomous, passive disturbance regulation to ensure a smooth flow rate in a flow circuit. Such regulation would have been difficult, if not impossible, for an active controller for a massively parallelized system involving possible multiple flow rate deviations in each line. In contrast, the passive regulation provided by the damper designed in this work allows for a smooth and (nearly) constant flow rate in each of the parallel lines effortlessly.

CONCLUSION

We have presented the design, assembly and operation of an eight-fold parallelized triphasic segmented flow reactor network for continuous nanoparticle-catalysed hydrogenations with complete online catalyst recovery and recycle. To do this, the detailed design of the fluid distribution manifolds that not only enable equal distribution into each arm of the reactor network, but also allow nearly complete damping of flow pulsations (to <1% of the total flow rate) introduced by the pumping mechanism is presented in Sections 2-5. This design framework is general, and the use of facile inline capacitive damping allows for robust autonomous operation of reactive (or non-reactive) microfluidic networks. The ability to continuously recover and recycle precious metal catalyst, enabled by catalyst 'immobilization' in liquid drops moving through the reactor network, opens up new avenues for both catalyst screening for a wide variety of intensified gas-liquid reactions and for robust, continuous scaled-up operation. Further work on this system will focus on pushing the limits of reactor channel dimensions, in order to enable further increases in productivity whilst retaining the highly intensified segmented flow regime.

The design of the inline hydraulic damper for parallelized system can be used in many operations such as in an industrial production wherein the one-to-many splitting of a fluid stream is required. The design of the parallelized millireactor system can be applied in organic syntheses in pharmaceutical and fine chemical industries, as well as for the production of materials using small-scale flowing reactors. Many reactions are conducted using macro-scale reactors such as stirred batch reactors, trickle bed reactors as well as plug flow reactors. These macro-scale reactors are often faced with heat and mass transfer limitations due to low specific interfacial area. Such limitations can be mitigated through the use of micro-/milli-reactors as platforms for organic and material syntheses due to the tremendous transport acceleration inherent in these small scale flowing systems. However, the throughput of a single small-scale flowing reactor is limited. Consequently, the operation of micro-/milli-reactors in parallel is required for high throughput productions. The design of a proper flow distributor to direct stable flow feed streams into each reactor operating in parallel is thus essential for the smooth operation of parallelized reactor systems.

Whilst there has been described in the foregoing description preferred embodiments of the present invention, it will be understood by those skilled in the technology concerned that many variations or modifications in details of design or construction may be made without departing from the present invention.

The invention claimed is:

1. A multiphase reactor system for performing multiphase reactions, the reactor system comprising:
   (a) a plurality of millitube reactors, each millitube reactor comprises a first end, a second end, a first chamber attached to the first end, and a second chamber disposed between the two ends of the millitube;
   (b) a first feed line comprising a first end and a second end, the first end for receiving a first liquid, a first level junction connected to the second end, and a first hydraulic damper disposed between the two ends of the first feed line;
   (c) a second feed line comprising a first end and a second end, the first end for receiving a second liquid, a first level junction connected to the second end, and a second hydraulic damper disposed between the two ends of the second feed line;
   (d) a third feed line comprising a first end and a second end, the first end for receiving a gas, and a first level junction connected to the second end,
   wherein,
      (a) the first level junction in each of the first, second and third feed line forks each feed line into y-number of feed lines,
      (b) each of the y-number of feed lines from the first level junction of the first feed is connected in fluid communication with the first chamber of the millitube reactor, each of the y-number of feed lines from the first level junction of the second feed is connected in fluid communication with the second chamber, and each of the y-number of feed lines from the first level junction of the third feed is connected in fluid communication with the third chamber,
      (c) the first chamber of the millitube reactor is capable of receiving both the first and second liquids, and the second chamber is capable of receiving both a gas and a mixture of the first and second liquids, and
      (d) y is an integer greater or equal to 2.

2. The multiphase reactor system of claim 1, wherein each feed line from the first level junction further comprises a second level junction for forking each feed line into further two feed lines.

3. The multiphase reactor system of claim 2, wherein each feed line from the second level junction further comprises a third level junction for forking each feed line into further two feed lines.

4. The multiphase reactor system of claim 3, further comprising n-level junctions for providing a plurality of first, second and third feed lines connected in fluid communication with a plurality of millitube reactors, the plurality of millitube reactors connected in parallels, wherein n is an integer greater or equal to 1.

5. The multiphase reactor system of claim 4, wherein the second ends of two millitube reactors converge into one output stream at a junction.

6. The multiphase reactor system of claim 5, wherein the output streams from the millitube reactors converge into one output stream.

7. The multiphase reactor system of claim 1, further comprising:
   (a) a first liquid container connected to the first end of the first feed line, the first container connected in fluid communication to a first pump;
   (b) a second liquid container connected to the first end of the second feed line, the second container connected in fluid communication to a second pump;
   (c) a gas container connected to the first end of the third feed line; and
   (d) an outflow container connected to the second end of the millitube.

8. The multiphase reactor system of claim 7, wherein the first and second pumps are each a peristaltic pump.

9. The multiphase reactor system of claim 1, wherein the millitube reactor has a length of about 2 to 20 m and an inner diameter of about 1 to 5 mm.

10. The multiphase reactor system of claim 1, wherein the hydraulic damper comprises a first tube, a second tube, and a third tube that are connected in series, the second tube having an inner diameter larger than that of the first tube and that of the third tube.

11. The multiphase reactor system of claim 10, wherein the first tube has the same length and inner diameter as those of the third tube.

12. The multiphase reactor system of claim 10, wherein the second tube is an elastic sleeve.

13. The multiphase reactor system of claim 12, wherein the second tube has an inner diameter of 4.76 mm and a length of 8 cm.

14. The multiphase reactor system of claim 12, wherein the second tube is made of silicone.

15. The multiphase reactor system of claim 1, wherein the millitube is a polytetrafluoro-ethylene tube, a polyether ether ketone tube, a fluorinated ethylene propylene tube, a glass tube, or a metal tube.

\* \* \* \* \*